United States Patent [19]
Egbertson et al.

[11] Patent Number: 5,990,107
[45] Date of Patent: Nov. 23, 1999

[54] FIBRINOGEN RECEPTOR ANTAGONIST PRODRUGS

[75] Inventors: Melissa S. Egbertson, Ambler; George D. Hartman, Lansdale; William C. Lumma, Pennsburg; John S. Wai, Harleysville; Steven D. Young, Lansdale, all of Pa.

[73] Assignee: Merck & Co., Inc., Rahway, N.J.

[21] Appl. No.: 08/883,114

[22] Filed: Jun. 26, 1997

Related U.S. Application Data

[60] Provisional application No. 60/020,976, Jun. 28, 1996.
[51] Int. Cl.⁶ .......................... A01N 43/58; A01N 43/40; C07D 237/26; C07D 211/68
[52] U.S. Cl. .......................... 514/250; 514/255; 514/318; 514/326; 544/234; 544/344; 544/360; 546/193; 546/194
[58] Field of Search ..................................... 544/234, 344, 544/360; 546/194, 193; 514/250, 318, 255, 326

[56] References Cited

U.S. PATENT DOCUMENTS

| | | | |
|---|---|---|---|
| 5,256,812 | 10/1993 | Alig et al. | 560/35 |
| 5,547,671 | 8/1996 | Duthinh | 424/195.1 |
| 5,814,636 | 9/1998 | Katano et al. | 514/252 |

FOREIGN PATENT DOCUMENTS

| | | |
|---|---|---|
| 659 743 A1 | 6/1995 | European Pat. Off. . |
| 6597843 | 6/1995 | European Pat. Off. . |
| 718 287 A2 | 12/1995 | European Pat. Off. . |
| 44 46 301 A1 | 12/1994 | Germany . |
| WO 94 22834 | 10/1994 | WIPO . |
| WO 94/22835 | 10/1994 | WIPO . |

*Primary Examiner*—Mukund J. Shah
*Assistant Examiner*—Tamthom N. Truong
*Attorney, Agent, or Firm*—Richard S. Parr; Melvin Winokur

[57] ABSTRACT

Fibrinogen receptor antagonist alcohol prodrugs having the structure, for example, of

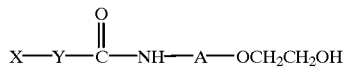

more particularly,

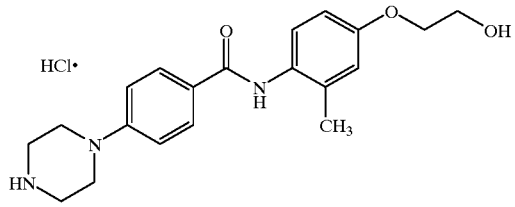

and

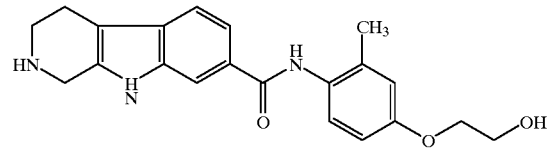

11 Claims, No Drawings

FIBRINOGEN RECEPTOR ANTAGONIST PRODRUGS

This application claims the benefit of U.S. Provisional Application No. 60/020,976, filed Jun. 28, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Haverstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., J. Biol Chem., 262, 16157–16163 (1987); Huang et al., Biochemistry, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. USA, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-polypeptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,812 discloses compounds of the $R^1$—A—$(W)_a$—X—$(CH_2)_b$—$(Y)_c$—B—Z—COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonist prodrugs of antagonists that have significant binding activity and are, therefore, useful for the reasons stated herein.

SUMMARY OF THE INVENTION

The invention relates to compounds having the formula

X'—A—B and pharmaceutically acceptable salts, wherein

X' is a moiety, comprising between 8 and 11 contiguous atoms selected from carbon and nitrogen, terminating at the non-A bond end in an amino, aliphatic amino, aromatic amino, amidino, or guanidino substituent having a pKa of between about 5–14, wherein the atom attached to A is selected from carbon and nitrogen;

A is
  a 5 or 6 membered aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl, or
  a 9 or 10 membered fused aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl; and B is
  —O $(CH_2)_n CH_2 OR^8$,
  —$CH_2(CH_2)_m CH_2 OR^8$, or $$-\underset{R^7}{\overset{}{C}}H(CH_2)_m CH_2 OR^8,$$

wherein n is 1 or 2, and m is 0, 1, or 2;
  $R^7$ is selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl;
  $R^8$ is selected from the group consisting of
  hydrogen,
  —C(O)—$C_{1-8}$alkyl,
  —C(O)—$C_{3-8}$cycloalkyl,
  —C(O)-aryl, and
  —C(O)—$C_{1-3}$alkylaryl.

The compounds are useful as prodrugs of fibrinogen receptor antagonists.

The invention also includes the use of a compound of the invention, or a pharmaceutically acceptable salt thereof, in the manufacture of a medicament for inhibiting the aggregation of blood platelets, preventing platelet thrombosis, preventing thromboembolism or preventing reocclusion, in a mammal.

DETAILED DESCRIPTION OF THE INVENTION

The invention relates to compounds having the formula $$X'\text{—}A\text{—}B$$

and pharmaceutically acceptable salts, wherein

X' is a moiety, comprising between 8 and 11 contiguous atoms selected from carbon and nitrogen, terminating at the non-A bond end in an amino, aliphatic amino, aromatic amino, amidino, or guanidino substituent having a pKa of between about 5–14, wherein the atom attached to A is selected from carbon and nitrogen;

A is
- a 5 or 6 membered aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl, or
- a 9 or 10 membered fused aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl; and B is
  —$(CH_2)_n CH_2 OR^8$,
  —$CH_2(CH_2)_m CH_2 OR^8$, or $$\text{—}\underset{\underset{R^7}{|}}{CH}(CH_2)_m CH_2 OR^8,$$

wherein n is 1 or 2, and m is 0, 1, or 2;

$R^7$ is selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl;

$R^8$ is selected from the group consisting of
  hydrogen,
  —C(O)—$C_{1-8}$alkyl,
  —C(O)—$C_{3-8}$cycloalkyl,
  —C(O)-aryl, and
  —C(O)—$C_{1-3}$alkylaryl.

In one class of the invention, the compound has the formula $$X\text{—}Y\text{—}Z\text{—}A\text{—}B$$

and pharmaceutically acceptable salts, wherein

X is
- a 5, 6 or 7 membered aromatic or nonaromatic ring, having 1, 2 or 3 heteroatoms selected from N, O, and S, and either unsubstituted or monosubstituted on carbon and nitrogen atoms with $R^1$ or disubstituted with $R^1$ and $R^2$, where $R^1$ and $R^2$ are independently selected from the group consisting of hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl, or
a 9 or 10 membered fused aromatic or nonaromatic ring, having 1, 2 or 3 heteroatoms selected from N, O, and S, and either unsubstituted or monosubstituted on carbon and nitrogen atoms with $R^1$ or disubstituted with $R^1$ and $R^2$, where $R^1$ and $R^2$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl;

Y is
a 5 or 6 membered aromatic or nonaromatic ring, having 0, 1, 2 or 3 heteroatoms selected from N, O, and S, and either unsubstituted or substituted on carbon and nitrogen atoms with $R^3$ selected from the group consisting of
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl; or
X and Y combined together form the structure

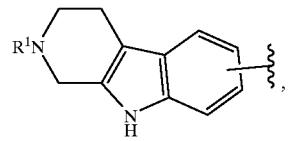

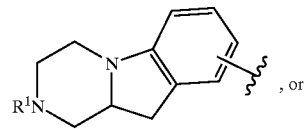, or

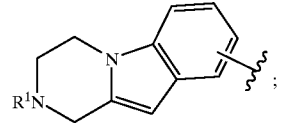;

Z is

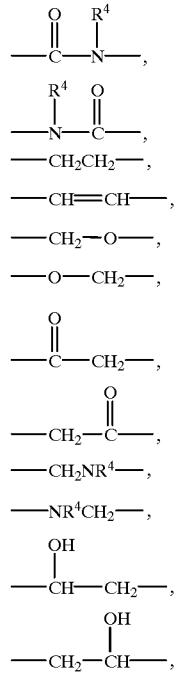

Z represents a bond;
$R^4$ is selected from the group consisting of hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

A is
  a 5 or 6 membered aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl, or
  a 9 or 10 membered fused aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl;

B is
  —O$(CH_2)_n CH_2 OR^8$,
  —$CH_2(CH_2)_m CH_2 OR^8$, or $$\underset{R^7}{-CH(CH_2)_m CH_2 OR^8,}$$

wherein n is 1 or 2, and m is 0, 1, or 2;
$R^7$ is selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl;
$R^8$ is selected from the group consisting of
  hydrogen,
  —C(O)—$C_{1-8}$alkyl,
  —C(O)—$C_{3-8}$cycloalkyl,
  —C(O)-aryl, and
  —C(O)—$C_{1-3}$alkylaryl.

In a subclass of the class, the compounds have the formula

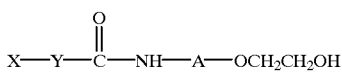

and pharmaceutically acceptable salts, wherein

X is a 6-membered aromatic or nonaromatic ring having 1, 2 or 3 nitrogen atoms;

Y is a 6-membered aromatic or nonaromatic ring having 0, 1, 2 or 3 nitrogen atoms;

A is a 6-membered aromatic ring unsubstituted, mono-substituted with a moiety selected from the group consisting of halogen, $C_{1-3}$alkyl, and $C_{1-3}$alkylsulfonylamino, disubstituted with one or more moieties, same or different, selected from the group consisting of halogen, $C_{1-3}$alkyl, and $C_{1-3}$alkylsulfonylamino or trisubstituted with one or more moieties, same or different, selected from the group consisting of halogen, $C_{1-3}$alkyl, and $C_{1-3}$alkylsulfonylamino, and all other substituents are as previously defined.

In a group of this subclass, the compounds have the formula

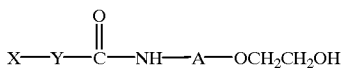

and pharmaceutically acceptable salts, wherein

X is a 6-membered aromatic or nonaromatic ring having 1 or 2 nitrogen atoms;

Y is a 6-membered aromatic or nonaromatic ring having 0 or 1 nitrogen atoms;

A is a 6-membered aromatic ring unsubstituted, mono-substituted with a moiety selected from the group consisting of Br, $CH_3$, and $NHSO_2CH_3$, disubstituted with one or more moieties, same or different, selected from the group consisting of Br, $CH_3$, and $NHSO_2CH_3$, or trisubstituted with one or more moieties, same or different, selected from the group consisting of Br, $CH_3$, and $NHSO_2CH_3$; and and all other substituents are as previously defined.

In a subgroup of this group, the compounds have the formula

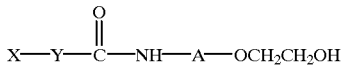

and pharmaceutically acceptable salts, wherein

X is

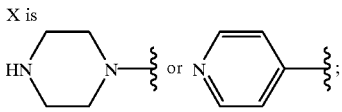

Y is

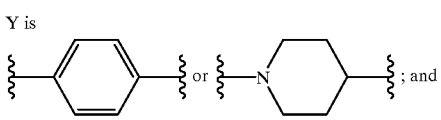

A is

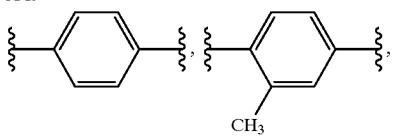

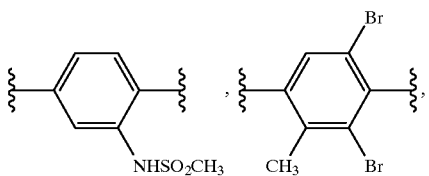

and all other substituents are as previously defined.

Examples of this subgroup include 2-(4-(4-(1-Piperazinyl)phenylcarbonylamino)phenoxy) ethanol, 2-(3-Methyl-4-(4-(1-piperazinyl)phenylcarbonylamino) phenoxy)-ethanol, 2-(4-(4-(4-Piperazin-1-yl)phenylcarbonylamino)-2-methanesulfonylaminophenoxy)ethanol, 2-(3-Methyl-4-(β-carbolin-7-yl-carboxamido)phenoxy) ethanol, 2-(2,6-Dibromo-3-methyl-4-(4-(piperizin-4-yl) phenylcarboxamide)phenoxy) ethanol, 4-(Pyridyl)(piperidin)-4-carbonylamino-3-methylphenoxyethanol and pharmaceutically acceptable salts, e.g. hydrochloride salts.

The active acids of these compounds have been evaluated in vitro and found to have an $IC_{50}$ for inhibiting platelet aggregation of between about 0.008 μM and 2 μM.

The prodrugs may be administered in low amounts relative to achieve inhibition of fibrinogen binding to the fibrinogen receptor. The prodrugs may be administered orally. The prodrugs retain structural integrity while passing though the gastrointestinal system, and are effectively delivered to cells. They are subjected to oxidative enzymes such as alcohol and aldehyde dehydrogenase to form the active acid which then interacts with the platelet receptor site.

A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the acids of the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor.

The IC$_{50}$ is the dose of a particular compound inhibiting aggregation by 50% relative to a control lacking the compound.

Additionally, these compounds are useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

Additionally, these compounds are useful for treating angiogenesis (formation of new blood vessels). It has been postulated that the growth of tumors depends on an adequate blood supply, which in turn is dependent on the growth of new vessels into the tumor. Inhibition of angiogenesis can cause tumor regression in animal models. (See, *Harrison's Principles of Internal Medicine*, 12th ed., 1991). These compounds are therefore useful in the treatment of cancer for inhibiting tumor growth. (See e.g., Brooks et al., *Cell*, 79:1157–1164 (1994)).

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Some of the compounds of the present invention are chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

The compounds of the invention are prodrugs of active acids which inhibit fibrinogen binding to the gpIIb/IIIa platelet receptor site. For example, these acids form in vivo, subsequent to administration to the patient, according to successive alcohol dehydrogenase and aldehyde dehydrogenase reactions:

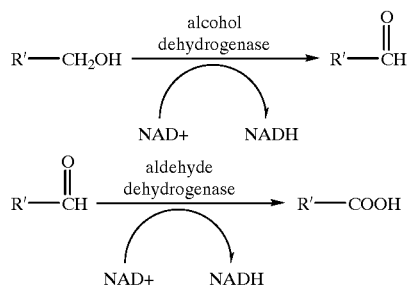

Other mechanisms may contribute to the conversion of alcohol to acid. Compounds of the invention of the general formula R'—CH$_2$OR$^8$, where R$^8$ is an acyl moiety, may be esters which metabolize into the active acid.

The invention also includes the use of a compound of the invention, or a pharmaceutically acceptable salt thereof, in the manufacture of a medicament for inhibiting the binding of fibrinogen to blood platelets, inhibiting the aggregation of blood platelets, treating thrombus formation or embolus formation, or preventing thrombus or embolus formation in a mammal.

The term "a moiety comprising between 8 and 11 contiguous atoms" means a series of sequentially bonded atoms, including a series of atoms that are sequentially bonded in linear relation, wherein none of the atoms are part of a cyclic moiety, and a series of atoms that are sequentially bonded in a linear relation, wherein some of the atoms are part of a cyclic moiety.

For example, the following is an example of 10 contiguous carbon or nitrogen atoms bonded in linear relation, wherein none of the atoms are part of cyclic moiety:

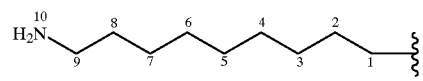

The following is an example of 10 contiguous carbon or nitrogen atoms bonded in linear relation, wherein 8 of the atoms are part of one or more cyclic moieties:

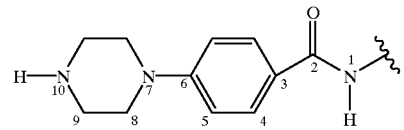

The following is an example of a structure having 11 contiguous carbon or nitrogen atoms (atoms numbered 1'–11') bonded in linear relation, wherein 7 of the atoms are part of one or more cyclic moieties:

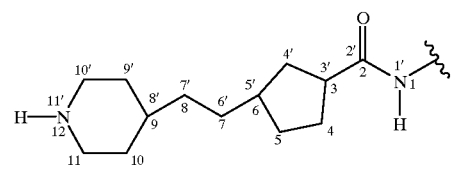

The above structure also has 12 contiguous carbon or nitrogen atoms (atoms numbered 1–12) bonded in linear relation, wherein 8 of the atoms are part of one or more cyclic moieties. Since the above structure has 11 contiguous carbon or nitrogen atoms bonded in linear relation, wherein 7 of the atoms are part of one or more cyclic moieties, the structure falls within the definition of X'.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen-substituted derivatives thereof.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-5}$ alkyl-carbonylamino is equivalent to

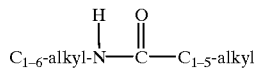

wherein the $C_{1-5}$alkyl moiety attaches to the substituted molecule.

In the schemes and examples below, various reagent symbols have the following meanings:
BOC
(or Boc): t-butyloxycarbonyl
Pd-C: palladium on activated carbon catalyst
DMF: dimethylformamide
DMSO: dimethylsulfoxide
CBZ: carbobenzyloxy
$CH_2Cl_2$: methylene chloride
$CHCl_3$: chloroform
EtOH: ethanol
MeOH: methanol
EtOAc: ethyl acetate
HOAc: acetic acid
BOP: benzotriazol-1-yloxytris(dimethylamino) phosphonium, hexafluorophosphate
EDC: 1-(3-dimethylaminopropyl)-3-ethylcarbodiimide hydrochloride
Oxone: potassium peroxymonosulfate
LDA: lithium diisopropylamide
PYCLU: Chloro N,N,N'N'-bis(pentamethylene) formamidinium hexafluorophosphate The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. For example, a typical 90 kg patient would receive oral dosages ranging between about 0.9 mg/day and about 9 g/day, most preferably between about 0.9 mg/day and 1.8 g/day. Suitable pharmaceutical oral compositions such as tablets or capsules may contain 10–500 mg, for example, 10 mg, 100 mg, 200 mg and 500 mg. Intravenously, the most preferred doses will range from about 1 to about 10 mg/kg/minute during a constant rate infusion.

Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail form the active ingredient of the prodrug, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active ingredient prodrug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral prodrug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

In the examples below, field strength for NMR analysis is either 300 MHz or 400 MHz.

In one general procedure for making compounds of the invention, 4-aminophenol is reacted with halogenated ethanol to produce 4-aminophenoxy ethanol, which is combined with a piperazinyl benzoic acid to produce an alcohol prodrug of the invention.

In another general procedure, 4-aminomethylphenol is combined with halogenated ethyl acetate to form ethyl 4-amino-3-methylphenoxyacetate, which is then reacted with halogenated ethanol to produce a 3-methyl-4-aminophenoxyethanol. The 3-methyl-4-aminophenoxyethanol is reacted with piperazinyl benzoic acid to produce an alcohol prodrug of the invention.

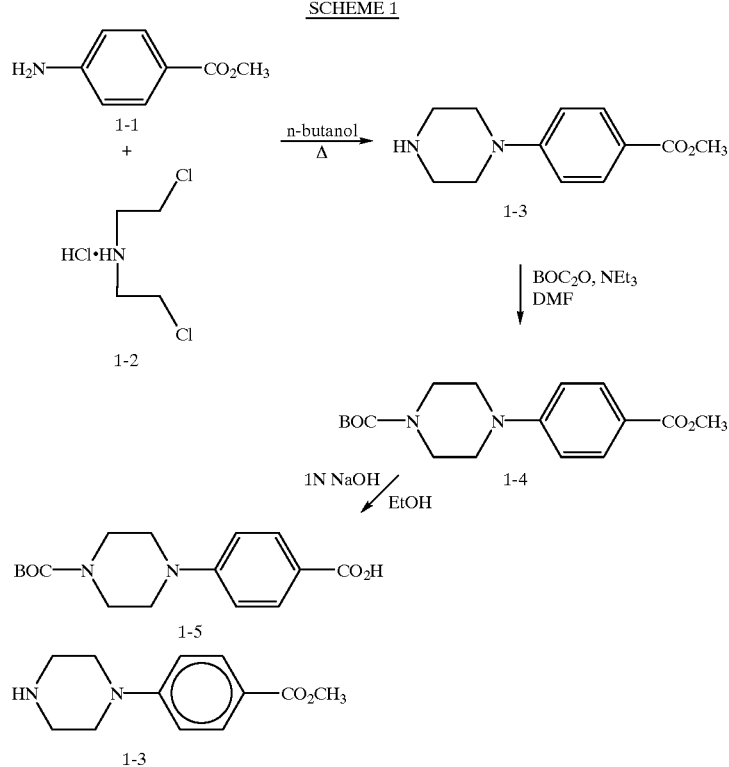

SCHEME 1

Methyl 4-(N-piperazinyl)benzoate (1-3)

A solution of amine 1-1 (20.0 g, 132 mmol), amine 1-2 (23.6 g, 132 mmol) and n-butanol (500 ml) was refluxed for 168 h. The solution was allowed to cool to ambient temperature. The crystals were collected, washed with Et$_2$O and dried in vacuo to give ester 1-3 as a white solid.

$^1$H NMR (CD$_3$OD): δ 7.86 (d, J=9 Hz, 2H), 7.98 (d, J=9 Hz, 2H), 3.78 (s, 3H), 3.53 (m, 4H), 3.31 (m, 4H).

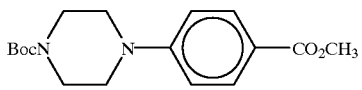

Methyl 4-(4-(1,1-dimethylethoxycarbonyl)piperazin-1-yl)benzoate (1-4)

To a stirred solution of amine 1-3 (15.0 g, 61.1 mmol), NEt₃ (7.42 g, 73.4 mmol) and DMF (150 ml) was added Boc₂O (14.7 g, 67.2 mmol). After 1.0 h, the solution was diluted with EtOAc and then washed with H₂O, 10% KHSO₄, brine, dried (MgSO₄) and concentrated to furnish ester 1-4 as a yellow solid.

TLC $R_f$=0.63 (silica, 40% EtOAc/hexanes); ¹H NMR (CD₃OD): δ 7.91 (d, J=9 Hz, 2H), 7.01 (d, J=9 Hz, 2H), 3.88 (s, 3H), 3.59 (m, 4H), 3.38 (m, 4H).

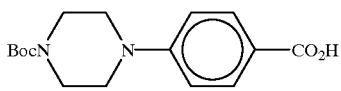

4-(4-(1,1-Dimethylethoxycarbonyl)piperazin-1-yl)benzoic acid (1-5)

A solution of ester 1-4 (21.1 g, 61.1 mmol) 1 N NaOH (100 ml, 100 mmol) and EtOH (200 ml) was heated to 60° C. for 2.0 h. The solution was acidifed with 10% KHSO₄ and then extracted with EtOAc. The EtOAc phase was washed with brine, dried (MgSO₄) and concentrated to furnish acid 1-5 as a white solid.

¹H NMR (CD₃OD): δ 7.81 (d, J=9 Hz, 2H), 6.88 (d, J=9 Hz, 2H), 3.49 (m, 4H), 3.24 (m, 4H), 1.40 (s, 9H).

SCHEME 2

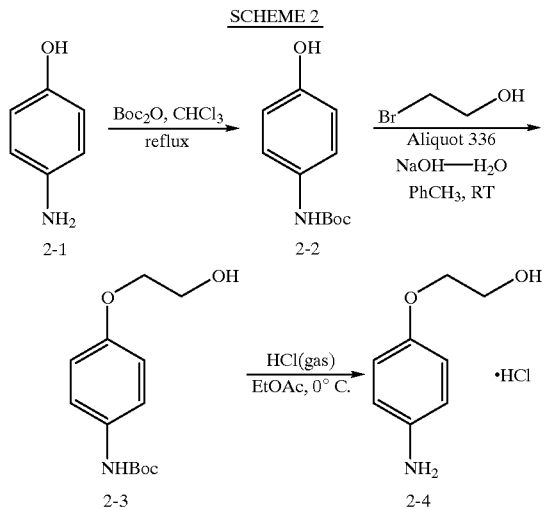

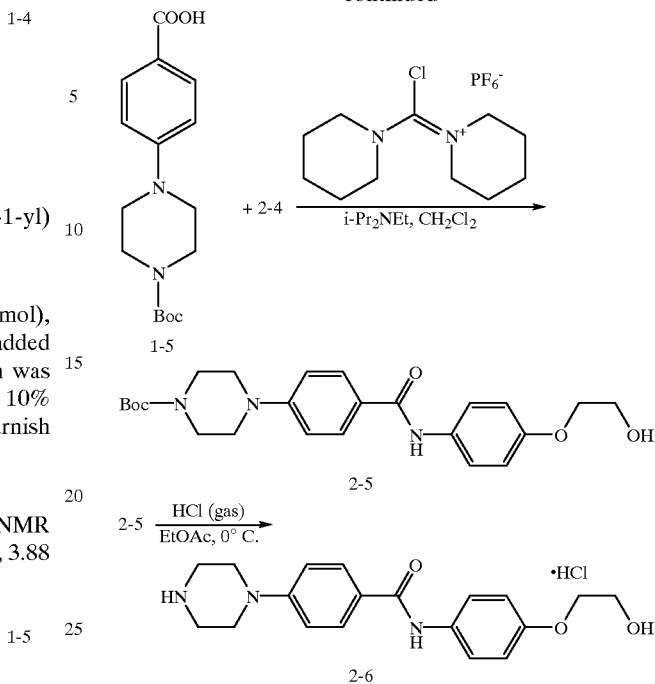

4-(1,1-Dimethylethoxycarbonyl)aminophenol (2-2)

To a 500 mL round bottomed flask with a stirring bar, reflux condenser and an argon inlet was added 4-aminophenol (10.00 g, 91.6 mmol), di-tert-butylpyrocarbonate (20.00 g, 91.6 mmol) and CHCl₃ (250 mL). This heterogeneous mixture was heated at reflux for 6 h during which time all of the solids dissolved. The mixture was cooled to room temperature and the solid product was collected by filtration. The material was triturated with a mixture of EtOAc-hexanes (1:2), collected on a frit and dried in vacuo to give 4-(1,1-dimethylethoxycarbonyl) aminophenol (2-2), mp: 143–144° C.

¹H NMR (CDCl₃): δ 1.51 (s, 9H), 5.27 (br s, 1H), 6.34 (br s, 1H), 6.73 (d, j=8.5 Hz, 2H), 7.16 (d, j=8.5 Hz, 2H).

2-(4-(1,1-Dimethylethoxycarbonyl)aminophenoxy)ethanol (2-3)

To a 500 mL round bottomed flask with a stirring bar and an argon inlet was added aqueous NaOH (50 mL of a 5N solution), 4-(1,1-Dimethylethoxycarbonyl)aminophenol (5.00 g, 23.90 mmol), toluene (100 mL), Aliquot 336 (0.88 g, 2.19 mmol), and 2-bromoethanol (1.86 mL, 26.29 mmol). This mixture was stirred vigorously at ambient temperature for 4 h. An additional 2 mL of 2-bromoethanol was added, and the reaction was continued for a total of 72 h. The mixture was diluted with EtOAc and the layers were separated. The organic phase was washed with water and brine. Drying (MgSO₄), filtration and removal of the solvent in vacuo gave 5.2 g of an oil. This material was chromatographed on 100 g of silica gel using 35% EtOAc-hexane as eluant. 2-(4-(1,1-dimethylethoxycarbonyl)aminophenoxy) ethanol was obtained as white needles.

¹H NMR (CDCl₃): δ 1.51 (s, 9H), 2.02 (t, j=6.2 Hz, 1H), 3.93 (m, 2H), 4.05 (m, 2H), 6.35 (br s, 1H), 6.86 (d, j=9.0 Hz, 2H), 7.26 (d, j=9.0 Hz, 2H).

2-(4-Aminophenoxy)ethanol, hydrochloride (2-4)

To a 200 mL round bottomed flask with a gas dispersion tube was added a solution of 2-(4-(1,1-dimethylethoxycarbonyl)aminophenoxy)ethanol (2.15 g, 8.49 mmol) in EtOAc (100 mL). This solution was cooled in an ice bath and dry HCl gas was sparged through the solution, vigorously, for 5 min. The resulting mixture was aged for 15 min. at 0° C. The excess HCl and solvent were removed in vacuo and the product was triturated with 50 mL of EtOAc and collected on a frit. The crystals were washed with additional EtOAc and dried in vacuo to give 1.26 g of 2-(4-aminophenoxy)ethanol, hydrochloride (76%).

$^1$H NMR (CD$_3$OD): δ 3.88 (t, j=4.2 Hz, 2H), 4.08(t, j=4.2 Hz, 2H), 7.07 (d, j=9.0 Hz, 2H), 7.32 (d, j=9.0 Hz, 2H).

2-(4-(4-(1-(1,1-Dimethylethoxycarbonyl)piperazinyl) phenylcarbonylamino)phenoxy)ethanol (2-5)

To a 100 mL round bottomed flask with a stirring bar and an argon inlet was added 4-(4-(1,1-dimethylethoxycarbonyl) piperazin-1-yl)benzoic acid (1.00 g, 3.26 mmol), 2-(4-aminophenoxy)ethanol hydrochloride (0.65 g, 3.43 mmol), chloro-N,N,N',N',-bis(pentamethylene)formamidinium hexafluorophosphate (1.24 g, 3.43 mmol), and CH$_2$Cl$_2$ (20 mL). This mixture was cooled in an ice bath and diisopropylethylamine (1.5 mL, 8.58 mmol) was added. The ice bath was allowed to expire and the solution was stirred at ambient temperature for 18 h. The CH$_2$Cl$_2$ was removed in vacuo and the residue was dissolved/suspended in 300 mL of EtOAc. This mixture was washed with 10% aqueous citric acid, saturated aqueous NaHCO$_3$, and brine. Drying (MgSO$_4$), filtration and removal of the solvent in vacuo gave a white solid. This material was chromatographed on 100 g of silica gel using 70% EtOAc-hexane as eluant. There was obtained 1.30 g of 2-(4-(4-(4-(1,1-dimethylethoxycarbonyl) piperazin-1-yl)phenyl)carbonylamino)phenoxy)ethanol as a crystalline solid.

$^1$H NMR (CDCl$_3$): δ 1.49 (s, 9H), 2.02 (br s, 1H), 3.28 (m, 4H), 3.59 (m, 4H), 3.96 (m, 2H), 4.09 (m, 2H), 6.93 (m, 4H), 7.52 (d, j=9.0 Hz, 2H), 7.78 (d, j=9.0 Hz, 2H).

2-(4-(4-(1-Piperazinyl)phenylcarbonylamino)phenoxy) ethanol, hydrochloride (2-6)

To a 1 L round bottomed flask equipped with a stirring bar and a gas dispersion tube was added 2-(4-(4-(4-(1,1-dimethylethoxycarbonyl)piperazin-1-yl) phenylcarbonylamino)phenoxy)ethanol (1.30 g, 2.94 mmol) and 500 mL of dry EtOAc. This well stirred suspension was cooled in an ice bath and HCl gas was sparged through the solution for 15 min. This mixture was aged 30 min. at 0° C. then the excess HCl was removed with a stream of argon and the EtOAc was removed in vacuo. The product was recrystallized from boiling MeOH/EtOAc (2x) to give 700 mg of 2-(4-(4-(1-piperazinyl)phenylcarbonylamino)phenoxy) ethanol, hydrochloride, mp: >260° C.

$^1$H NMR (DMSO-d$_6$): δ 3.31 (m, 4H), 3.56 (m, 4H), 3.81 (m, 2H), 4.02 (m, 2H), 4.40 (br s, 3H), 6.94 (d, j=9.0 Hz, 2H), 7.09 (d, j=9.0 Hz, 2H), 7.52 (d, j=9.0 Hz, 2H), 7.90 (d, j=9.0 Hz, 2H).

SCHEME 3

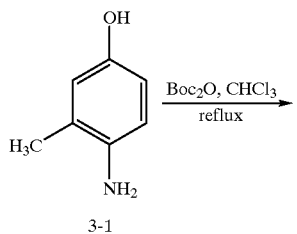

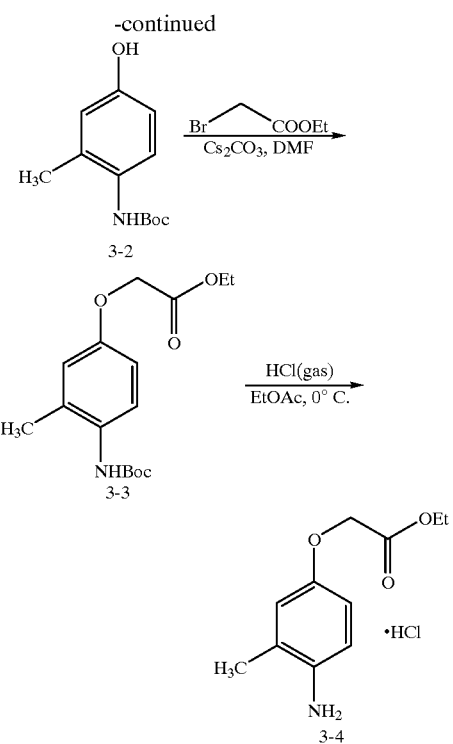

4-(1,1-dimethylethoxycarbonyl)amino-3-methylphenol (3-2)

To a 1 L round bottomed flask with a stirring bar, reflux condenser and an argon inlet was added 4-amino-3-methylphenol (15.00 g, 121.79 mmol), di-tert-butylpyrocarbonate (27.25 g, 124.84 mmol) and CHCl$_3$ (300 mL). This heterogeneous mixture was heated at reflux for 24 h during which time all of the solids dissolved. The mixture was cooled to room temperature and the solid product was collected by filtration. The material was triturated with a mixture of Et$_2$O-hexanes (1:1), collected on a frit and dried in vacuo to give 21.25 g (92%) of 4-(1,1-dimethylethoxycarbonyl)amino-3-methylphenol (3-2), mp: 143–144° C.

$^1$H NMR (CDCl$_3$): δ 1.51 (s, 9H), 2.14 (s, 3H), 6.08 (br s, 1H), 6.48 (m, 2H), 6.60 (br s, 1H), 7.20 (d, j=8.5 Hz, 1H). ps Ethyl 4-(1,1-dimethylethoxycarbonyl)amino-3-methylphenoxyacetate (3-3)

To a 200 mL round bottomed flask with a stirring bar, and an argon inlet was added 4-(1,1-dimethylethoxycarbonyl) amino-3-methylphenol (5.00 g, 22.39 mmol), Cs$_2$CO$_3$ (14.59 g, 44.78 mmol), DMF (50 mL), and ethyl bromoacetate (2.61 mL, 23.51 mmol). This mixture was stirred vigorously at ambient temperature for 24 h. The mixture was filtered through a frit and the DMF was removed under high vacuum. The residue was dissolved in EtOAc (300 mL) and washed with H$_2$O (2x) and brine (1x). Drying (MgSO$_4$), filtration, and removal of the solvent in vacuo gave a solid. This material was triturated with 5% Et$_2$O-hexane, the solid was collected by filtration and dried in vacuo to give 5.40 g (78%) of ethyl 4-(1,1-dimethylethoxycarbonyl)amino-3-methylphenoxyacetate as a white, crystalline solid.

$^1$H NMR (CDCl$_3$): δ 1.29 (t, j=7.2 Hz, 3H), 1.51 (s, 9H), 2.22 (s, 3H), 4.26 (q, j=7.2 Hz, 2H), 4.57 (s, 2H), 6.08 (br s, 1H), 6.72 (m, 2H), 7.56 (s, 1H).

Ethyl 4-amino-3-methylphenoxyacetate, hydrochloride (3-4)

To a 500 mL round bottomed flask with a gas dispersion tube was added a solution of ethyl 4-(1,1- dimethylethoxycarbonyl)amino-3-methylphenoxyacetate (5.31 g, 17.13 mmol) in EtOAc (200 mL). This solution was cooled in an ice bath and dry HCl gas was sparged through the solution, vigorously, for 10 min. The resulting mixture was aged for 15 min. at 0° C. The excess HCl gas was removed with a stream of argon and the solvent was removed in vacuo. The product was triturated with 50 mL of EtOAc and collected on a frit. The crystals were washed with additional EtOAc and dried in vacuo to give 4.21 g (100%) of ethyl 4-amino-3-methylphenoxyacetate, hydrochloride as white crystals, mp: 198–200° C.

$^1$H NMR (DMSO-d$_6$): δ 1.21 (t, j=7.1 Hz, 3H), 2.33 (s, 3H), 4.17 (q, j=7.1 Hz, 2H), 4.78 (s, 2H), 6.82 (dd, j=3,9 Hz, 1H), 6.92 (d, j=3 Hz, 1H), 7.39 (d, j=9 Hz, 1H), 10.21 (br s, 3H).

SCHEME 4

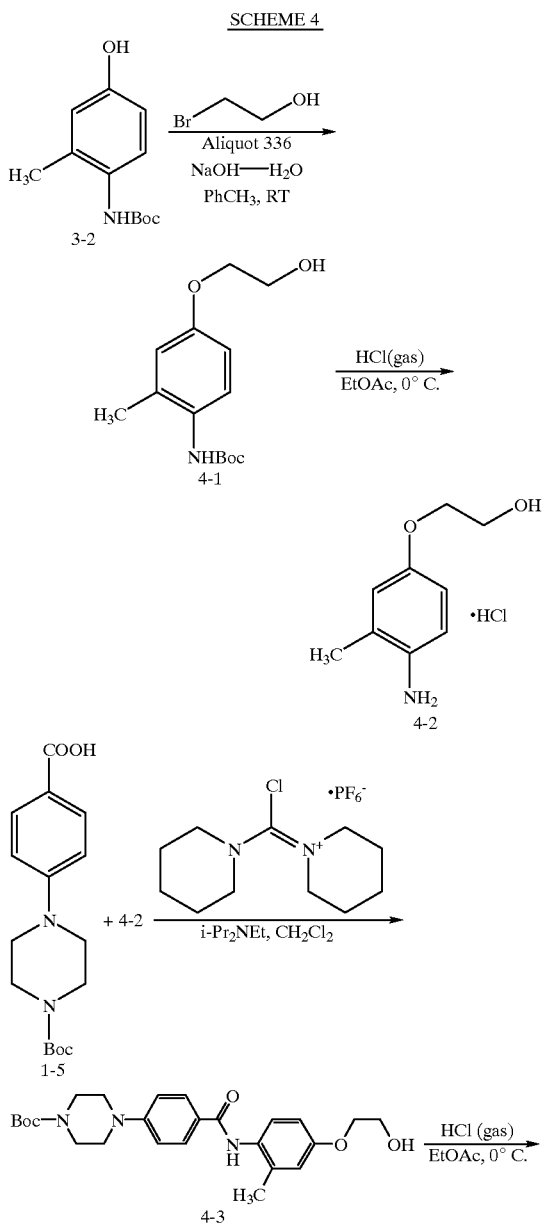

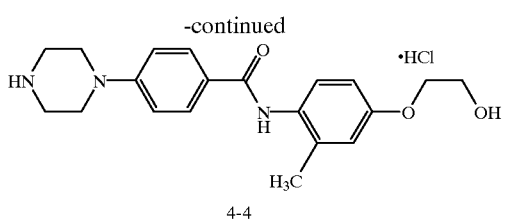

2-(3-Methyl-4-(1,1-dimethylethoxycarbonyl) aminophenoxy)ethanol (4-1)

In a manner similar to that described for compound 2-3, 2-(3-methyl-4-(1,1-dimethylethoxycarbonyl) aminophenoxy)ethanol was prepared.

$^1$H NMR (CDCl$_3$): δ 1.50 (s, 9H), 2.20 (s, 3H), 2.59 (t, j=6.1 Hz, 1H), 3.89 (m, 2H), 4.05 (m, 2H), 6.22 (br s, 1H), 6.69 (m, 2H), 7.48 (br s, 1H).

2-(3-Methyl-4-aminophenoxy)ethanol, hydrochloride (4-2)

In a manner similar to that described for compound 2-4, 2-(3-methyl-4-aminophenoxy)ethanol hydrochloride was prepared.

$^1$H NMR (DMSO-d$_6$): δ 2.33 (s, 3H), 3.69 (t, j=4.2 Hz, 2H), 4.04 (t, j=4.2 Hz, 2H), 4.58 (br s, 1H), 6.91 (m, 2H), 7.37 (d, j=9.0 Hz, 1H), 10.18 (br s, 3H).

2-(3-Methyl-4-(4-(1-(1,1-dimethylethoxycarbonyl) piperazinyl)-phenylcarbonylamino)phenoxy)ethanol (4-3)

In a manner similar to that described for compound 2-5, 2-(3-methyl-4-(4-(1-(1,1-dimethylethoxycarbonyl) piperazinyl)phenylcarbonyl-amino)phenoxy)ethanol was prepared.

$^1$H NMR (CDCl$_3$): δ 1.49 (s, 9H), 2.04 (br s, 1H), 2.28 (s, 3H), 3.28 (m, 4H), 3.59 (m, 4H), 3.96 (m, 2H), 4.08 (m, 2H), 6.79 (m, 2H), 6.92 (d, j=9.0 Hz, 2H), 7.46 (s, 1H), 7.67 (d, j=8.0 Hz, 1H), 7.80 (d, j=9.0 Hz, 2H).

2-(3-Methyl-4-(4-(1-piperazinyl)phenylcarbonylamino) phenoxy)-ethanol, hydrochloride (4-4)

In a manner similar to that described for compound 2-6, 2-(3-methyl-4-(4-(1-piperazinyl)phenylcarbonylamino) phenoxy)ethanol, hydrochloride was prepared, mp: >260° C.

$^1$H NMR (DMSO-d$_6$): δ 2.17 (s, 3H), 3.21 (m, 4H), 3.53 (m, 4H), 3.71 (t, j=5.2 Hz, 2H), 3.97 (t, j=5.2 Hz, 2H), 4.86 (br s, 1H), 6.76 (m, 1H), 6.83 (d, j=2.5 Hz, 1H), 7.06 (d, j=9.0 Hz 2H), 7.15 (d, j=8.4Hz, 1H), 7.89 (d, j=9.0 Hz, 2H), 9.40 (br s, 2H), 9.54 (s, 1H).

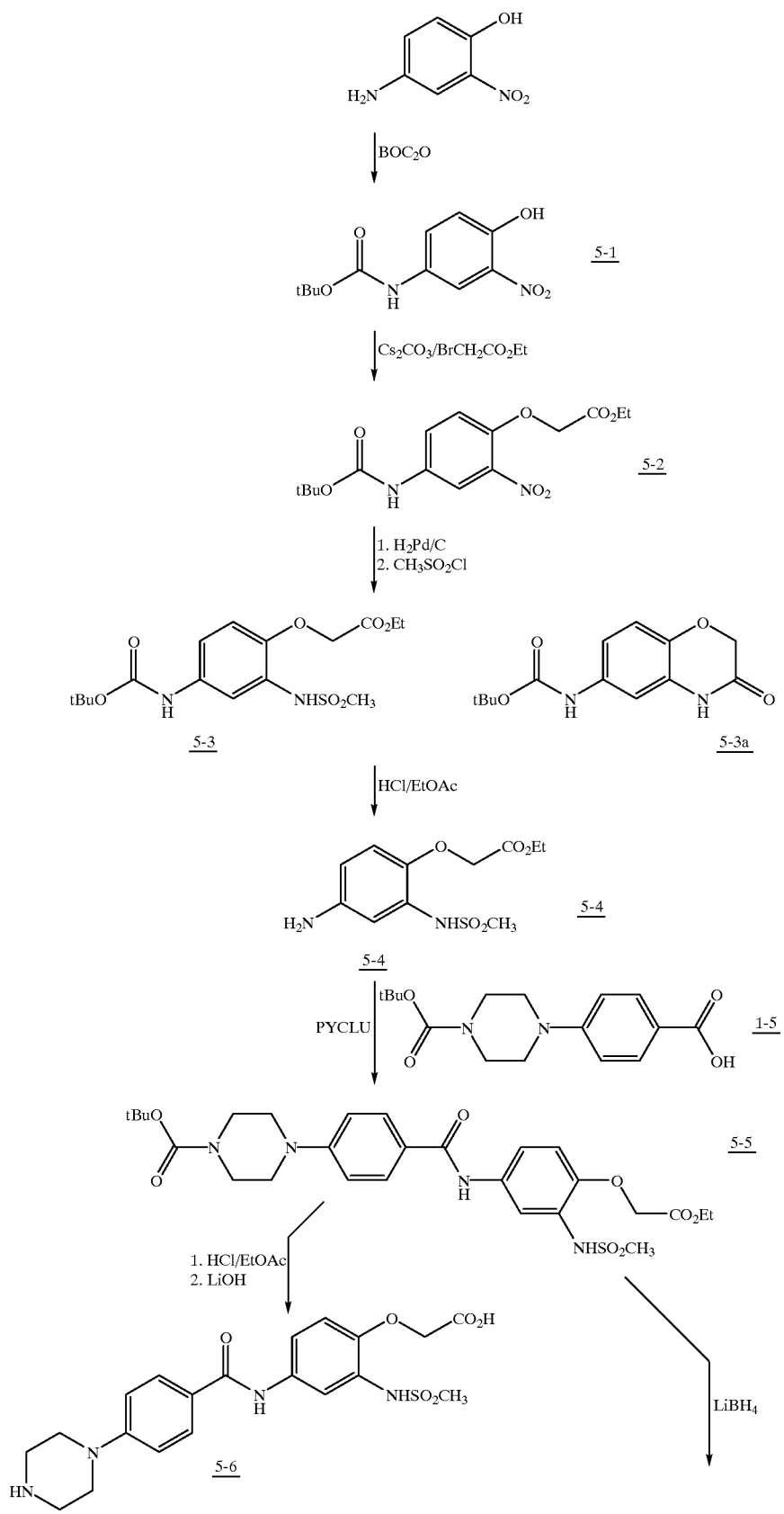

-continued
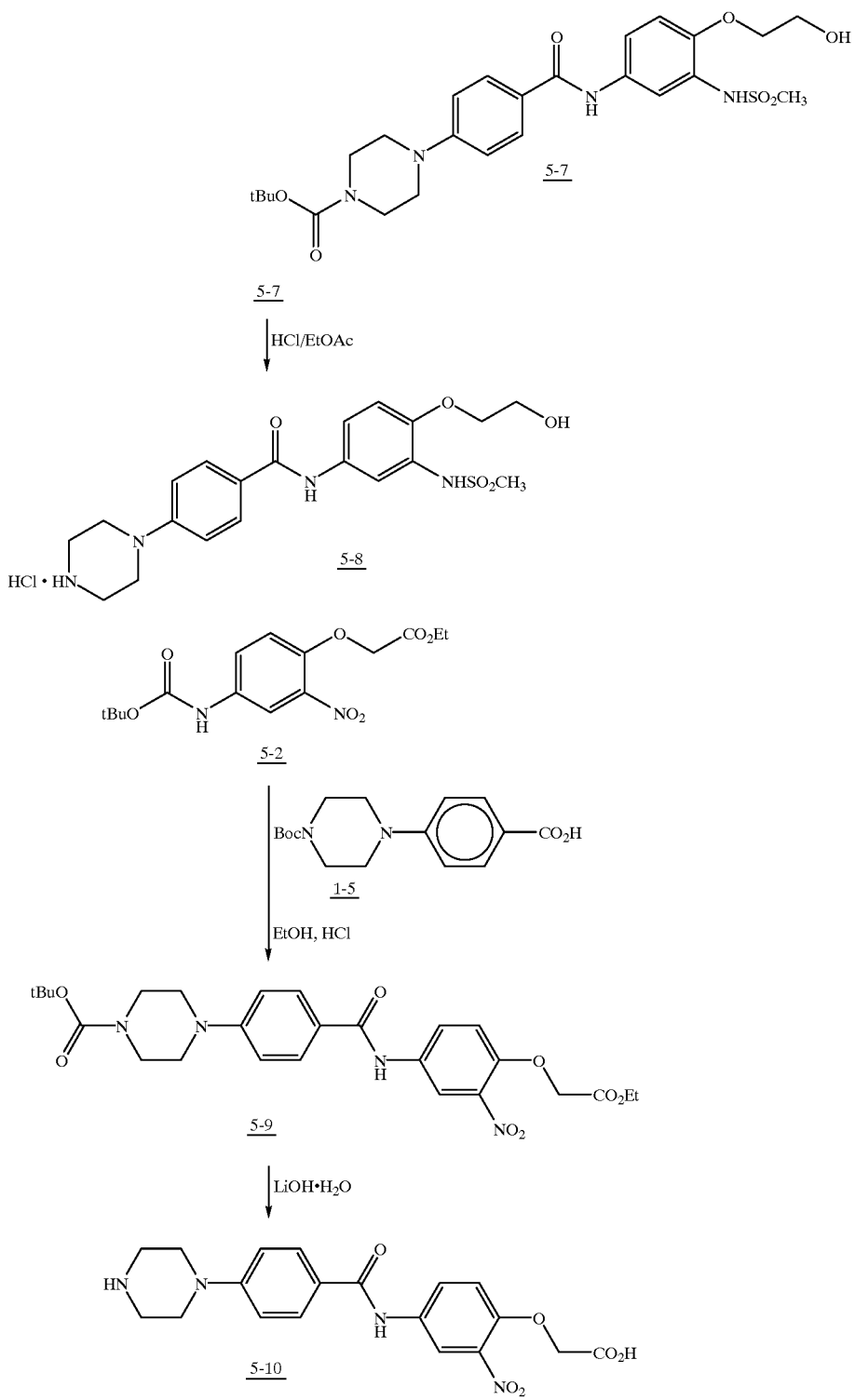

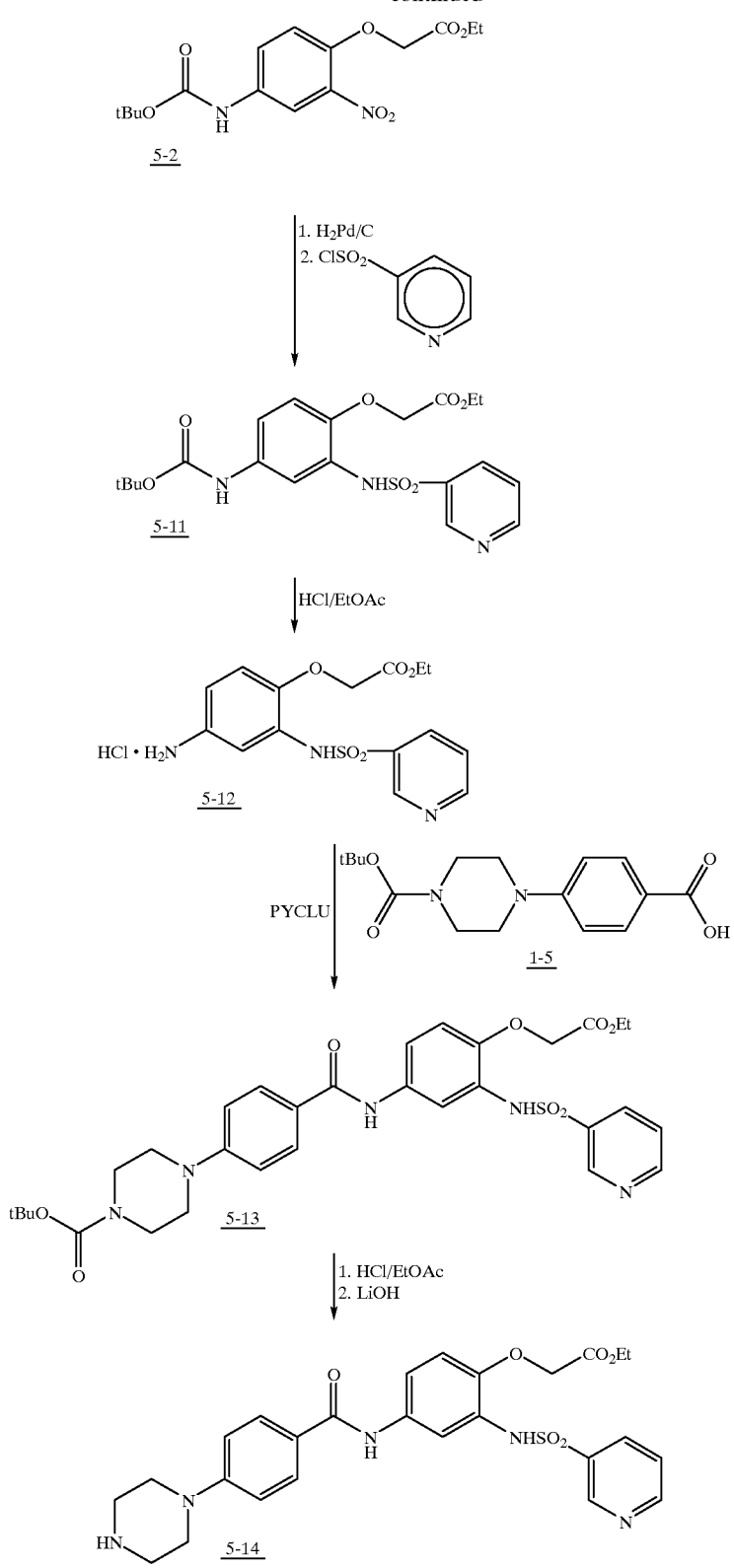

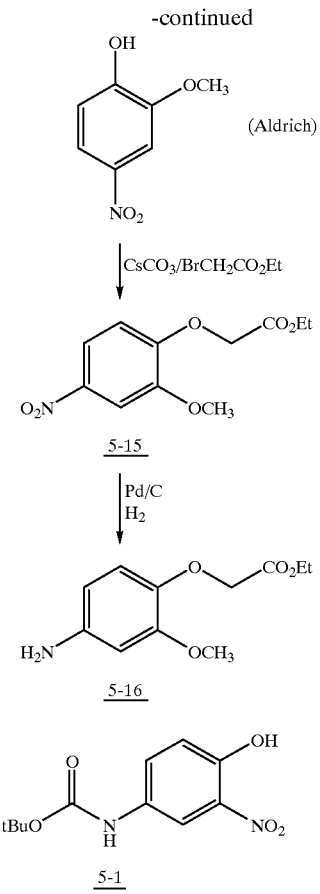

-continued

2-Nitro-4-(1,1-dimethylethoxycarbonylamino)phenol (5-1)

A solution of 2-nitro-4-amino phenol (Aldrich) (20 g, 130 mmol) in THF (500 mL) was cooled to 0° C. and treated with di-tert-butyldicarbonate (64 g, 293 mmol) and triethylamine (37 mL, 265 mmol). After 24 hours the solution was concentrated and the residue dissolved in EtOAc, washed with 10% $KHSO_4$, saturated $NaHCO_3$, and brine, dried over $Na_2SO_4$, filtered and evaporated. The crude bis-protected material ($R_f$ (40% EtOAc/Hexanes) 0.69) was then dissolved in 400 mL 1:1 THF/$H_2O$ and treated with LiOH.$H_2O$ (38 g, 1.3 mol). After stirring at room temperature overnight the solvent was removed and the residue was dissolved in EtOAc and washed with brine, dried with $Na_2SO_4$, filtered and concentrated to give 5-1 as a reddish, oily solid.

$R_f$(20% EtOAc/Hexanes)=0.41; $^1H$ NMR (400 MHz, $CDCl_3$) δ 10.35 (s, 1H), 8.18 (s, 1H), 7.58 (d, 1H), 7.13 (d, 1H), 6.45 (bs, 1H), 1.55 (s, 9H).

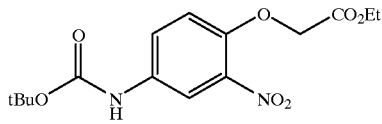

5-2

Ethyl 2-(2-nitro-4-(1,1-dimethylethoxycarbonylamino) phenoxy)acetate (5-2)

A solution of 5-1 (5 g, 19.7 mmol) in DMF (125 mL) was treated with cesium carbonate (3.17 g, 9.73 mmol), stirred for 10 minutes and treated with ethyl bromoacetate (2.2 mL, 19.8 mmol) at room temperature. After 1.5 hours the solution was concentrated under high vacuum and the residue was absorbed to silica gel and chromatographed in a gradient of 20 to 30% EtOAc/hexanes to give 5-2 as a bright yellow solid.

$R_f$(30% EtOAc/hexanes) 0.26; $^1H$ NMR (400 MHz, $CDCl_3$) δ 7.95 (s, 1H), 7.5 (d, 1H), 6.97 (d, 1H), 6.62 (bs, 1H), 4.72 (s, 2H), 4.25 (q, 2H), 1.5 (s, 9H), 1.28 (t, 3H).

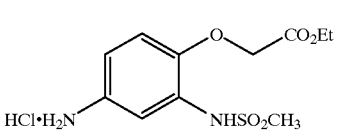

5-4

Ethyl (2-methanesulfonylamino-4-aminophenoxy)acetate hydrochloride (5-4)

A solution of 5-2 (2 g, 5.88 mmol) in EtOAc (25 mL) was treated with 10% Pd/C (0.67 g), and hydrogenated under balloon pressure for 1.5 hours. The solution was filtered through SolkaFloc, and the cake rinsed with EtOAc. The filtrate was not concentrated but was treated directly with methanesulfonyl chloride (3.0 mL, 39 mmol) and pyridine (5.0 mL, 62 mmol) and stirred overnight. The solution was concentrated and the residue was dissolved in EtOAc and washed with 10% $KHSO_4$, saturated $Na_2CO_3$, and brine, dried with $Na_2SO_4$, filtered and concentrated to give a yellow oil that was chromatographed (40% EtOAc/hexanes) to give 5-3 ($R_f$30% EtOAc/hexanes) 0.19) contaminated with 5-3a. The mixture (1.7 g) was dissolved in EtOAc (75 mL), cooled to −78° C. and saturated with HCl gas, warmed to 0° C. for 1 hour and concentrated. The residue was partitioned between $CH_2Cl_2$ and saturated $NaCO_3$, the layers separated and the aqueous layer extracted with $CH_2Cl_2$.

The organic layer was dried over Na₂SO₄, filtered and evaporated and the residue chromatographed (60% EtOAc/hexanes) to give 5-4 as an off-white solid.

R_f(60% EtOAc/hexanes)=0.3; ¹H NMR (400 MHz, CDCl₃) δ 7.7 (bs, 1H), 6.95 (s, 1H), 6.74 (d, 1H), 6.4 (d, 1H), 4.6 (s, 2H), 4.33 (q, 2H), 2.98 (s, 3H), 1.3 (t, 3H).

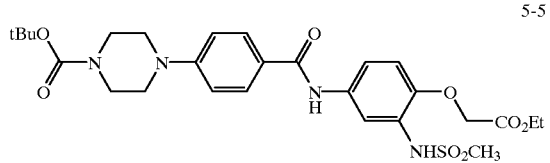

5-5

Ethyl 2-(4-(4-(4-(1,1-dimethylethoxycarbonyl)piperazin-1-yl)phenylcarbonylamino)-2'-methanesulfonylaminophenoxy)acetate (5—5)

A suspension of 5-4 (0.125 g, 0.433 mmol) and 1-5 (0.136 g, 0.444 mmol) in CH₂Cl₂ (4 mL) was treated with diisopropylamine (0.3 mL, 1.7 mmol) and PYCLU (0.173 g, 0.48 mmol) and stirred at room temperature for three days. The solution was concentrated and the residue was absorbed to silica gel and chromatographed in a gradient of 20 to 60% EtOAc/hexanes to give 5-5 as a pale yellow oil.

R_f (60% EtOAc/hexanes) 0.27; ¹H NMR (400 MHz, CDCl₃) δ 7.82 (dd, 1H), 7.79 (s, 1H), 7.77 (s, 1H), 7.54 (bs, 1H), 7.48 (s, 1H), 6.90 (m, 3H), 4.7 (s, 2H), 4.25 (q, 2H), 3.6 (m, 4H), 3.3 (m, 4H), 3.03 (s, 3H), 1.5 (s, 9H), 1.3 (t, 3H).

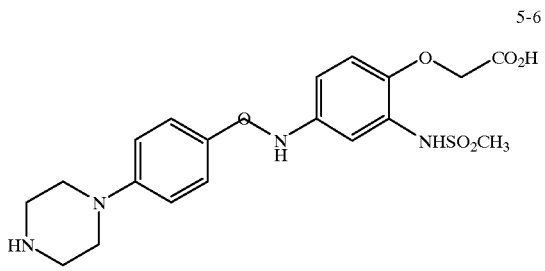

5-6

2-(4-(4-(Piperazin-1-yl)phenylcarbonylamino)-2'-methanesulfonylaminophenoxy)acetic acid (5-6)

A solution of 5-5 (0.093 g, 0.16 mmol) was dissolved in EtOAc (10 mL), cooled to −78° C. and saturated with HCl gas, warmed to 0° C. for 1 hour and concentrated. The resulting white solid was dissolved in 1:1:1 H₂O/THF/MeOH, treated with LiOH.H₂O (0.038 g, 0.9 mmol) and stirred at room temperature for 1 hour. The reaction was concentrated and chromatographed (18:1:1 EtOH/H2O/NH₄OH) to give a yellow oil that was diluted with CH₂Cl₂ and evaporated to give 5-6 as white solid.

R_f(9: 1:1 EtOH/H₂O/NH₄OH)=0.48; ¹H NMR (400 MHz, D₂O+NaOD) δ 7.74 (s, 1H), 7.72 (s, 1H), 7.21 (s, 1H), 7.07 (s, 1H), 7.05 (s, 1H), 6.9 (d, 1H), 6.74 (d, 1H), 4.38 (s, 2H), 3.15 (m, 4H), 2.85 (m, 7H).

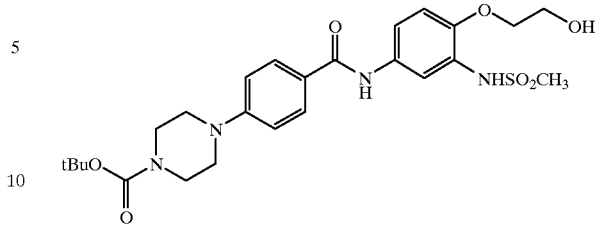

5-7

2-(4-(4-(4-(1,1-Dimethylethoxycarbonyl)piperazin-1-yl)phenylcarbonylamino)-2'-methanesulfonylaminophenoxy)ethanol (5-7)

A solution of 5-5 (0.196 g, 0.34 mmol) was dissolved in THF (5 mL), cooled to 0° C. and treated with LiBH₄ (2M in THF, 0.51 mL, 1.0 mmol) and allowed to warm to room temperature and stir overnight. The solution was poured into 10% KHSO₄ and extracted with EtOAc. The organic layer was washed with satruated NaHCO₃, brine, and dried over Na₂SO₄, filtered and evaporated. The residue was absorbed to silica gel and chromatographed in 100% EtOAc to give 5-7 as a white solid.

R_f(EtOAc)=0.28; ¹H NMR (400 MHz, CDCl₃+CD₃OD) δ 8.78 (s, 1H), 7.85 (s, 1H), 7.83 (s, 1H), 7.71 (d, 1H), 7.5 (s, 1H), 6.93 (m, 3H), 4.1 (m, 2H), 3.9 (m, 2H), 3.6 (m, 4H), 3.3 (m, 4H), 3.0 (s, 3H), 1.5 (s, 9H).

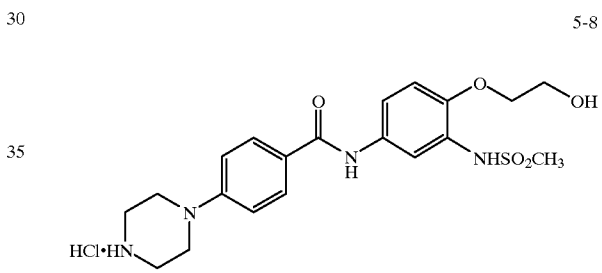

5-8

2-(4-(4-(4-Piperazin-1-yl)phenylcarbonylamino)-2'-methanesulfonylaminophenoxy)ethanol hydrochloride (5-8)

A solution of 5-7 (0.294 g, 0.466 mmol) was dissolved in EtOAc (10 mL), cooled to −78° C. and saturated with HCl gas, warmed to 0° C. for 1 hour and concentrated to give 5-8 as a white solid.

R_f(9: 1:1 EtOH/H₂O/NH₄OH)=0.67. ¹H NMR (400 MHz, D₂O+NaOD) δ 7.71 (s, 1H), 7.70 (s, 1H), 7.2 (s, 1H), 7.06 (s, 1H), 7.05 (s, 1H), 6.9 (m, 2H), 4.0 (m, 2H), 3.83 (m, 2H), 3.15 (m, 4H), 2.85 (m, 7H).

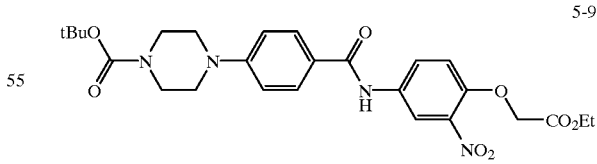

5-9

Ethyl 2-(4-(4-(4-(1,1-dimethylethoxycarbonyl)piperazin-1-yl)phenylcarbonylamino)-2'-nitrophenoxy)acetate (5-9)

A solution of 5-2 (0.3 g, 0.88 mmol) was dissolved in EtOAc (10 mL), cooled to −78° C. and saturated with HCl gas, warmed to 0° C. for 1 hour and concentrated to give ethyl 2-(2-nitro-4-aminophenoxy)acetic acid as a white solid that was coupled immediately (0.26 g, 0.88 mmol) to 1-5 (0.29 g, 0.95 mmol) as described for 5—5 to give 5-9 as a

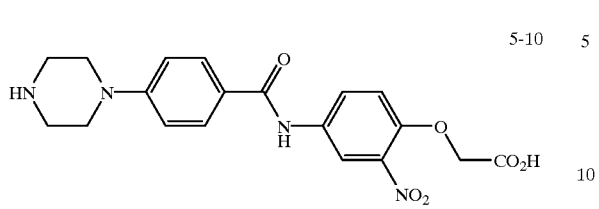

2-(4-(4-(Piperazin-1-yl)phenylcarbonylamino)-2'-nitrophenoxy)-acetic acid (5-10)

A solution of 5-9 (0.186 g, 0.352 mmol) in EtOAc was treated first with HCl gas then with LiOH.H₂O as described for 5-6 to give 5-10 as a yellow solid after chromatography in 18:1:1 EtOH/H₂O/NH₄OH).

$R_f$(18:1:1 EtOH/H2O/NH₄OH)=0.47; $^1$H NMR (400 MHz, D₂O) δ 8.0 (s, 1H), 7.68 (2s, 2H), 7.52 (d, 1H), 7.0 (m, 2H), 3.12 (bs, 4H), 2.85 (bs, 4H).

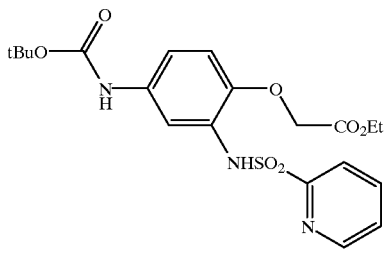

Ethyl (3-pyridylsulfonylamino-4-(1,1-dimethylethoxycarbonyl)-aminophenoxy)acetate (5-11)

A solution of 5-2 (2 g, 5.88 mmol) in EtOAc (25 mL) was treated with 10% Pd/C and 3-pyridylsulfonyl chloride (JOC, 1989, 54, 389–393) as described for 5-3 to give 5-11 after chromatography in a gradient of 30 to 50% EtOAc/hexanes as a white solid.

$R_f$(40% EtOAc/hexanes) 0.11 $^1$H NMR (400 MHz, CDCl₃) δ 9.02 (s, 1H), 8.71 (d, 1H), 8.1 (m, 2H), 7.4 (s, 1H), 7.33 (m, 2H), 6.69 (d, 1H), 6.58 (s, 1H), 4.4 (s, 2H), 4.23 (q, 2H), 1.5 (s, 9H), 1.25 (t, 3H).

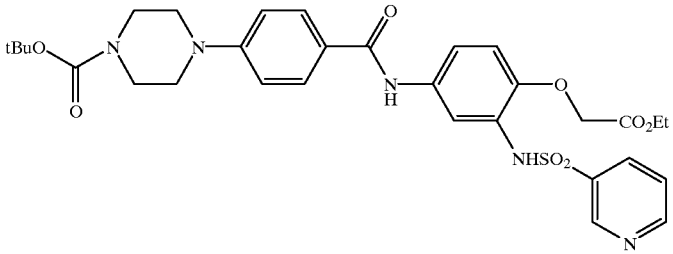

Ethyl 2-(4-(4-(4-(1,1-dimethylethoxycarbonyl)piperazin-1-yl)phenylcarbonylamino)-2'-(3-pyridvlsulfonylamino) phenoxy)acetate (5-13)

A solution of 5-11 (0.318 g, 0.704 mmol) in EtOAc (10 mL) was treated with HCl gas as described for 5-4 to give 5-12 as a white solid that was coupled directly with 1-5 as described for 5-5 to give 5-13 as a oily yellow solid after chromatography in a gradient of 20 to 40% acetone/hexanes.

$R_f$(50% EtOAc/hexanes) 0.41; $^1$H NMR (400 MHz, CDCl₃) δ

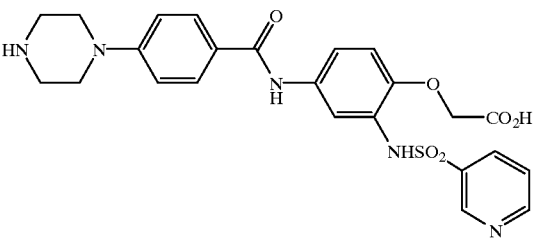

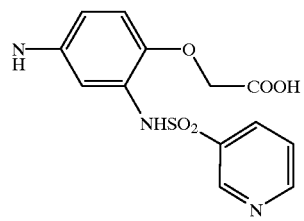

2-(4-(4-(Piperazin-1-yl)phenylcarbonylamino)-2'-(2-(3-pyridylsulfonylamino)phenoxy)acetate (5-14)

A solution of 5-13 (0.047 g, 0.087 mmol) in EtOAc was treated first with HCl gas then with LiOH.H₂O as described for 5-6 to give 5-14 as a yellow solid after chromatography in 18:1:1 EtOH/H₂O/NH₄OH).

$R_f$(18:1:1 EtOH/H₂O/NH₄OH) 0.38; $^1$H NMR (400 MHz, D₂O+NaOD) δ 8.76 (s, 1H), 8.5 (m, 1H), 8.13 (m, 1H), 7.7 (m, 2H), 7.45 (m, 1H), 7.12 (s, 1H), 7.08 (m, 2H), 6.84 (m, 1H), 6.67 (d, 1H), 4.13 (s, 2H), 3.25 (m, 4H), 2.87 (m, 4H).

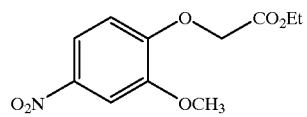

Ethyl (2-methoxy-4-nitrophenoxy)acetic acid (5-15)

2-Methoxy-4-nitrophenol (Aldrich) (1.0 g, 5.9 mmol) was treated with cesium carbonate and ethylbromoacetate as described for 5-2 to give crude 5-15 after removal of DMF. The crude material was partitioned between water and EtOAc, the organic layer was dried with brine and MgSO₄, filtered and evaporated to give 5-15 as a yellow solid.

$R_f$(50% EtOAc/hexanes)=O.54; $^1$H NMR (400 MHz, CDCl₃) δ 7.8 (d, 1H), 7.76 (s, 1H), 6.75 (d, 1H), 4.71 (s, 2H), 4.2 (q, 2H), 3.9 (s, 3H), 1.21 (t, 3H).

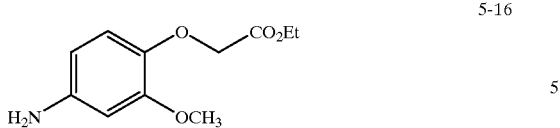
5-16

Ethyl (2-methoxy-4-aminophenoxy)acetic acid (5-16)

A solution of 5-15 (0.7 g, 2.7 mmol) in EtOH (10 mL) was treated with 10% Pd/C (0.14 g) and hydrogenated at balloon pressure. The solution was filtered through Solka-Floc and evaporated to give 5-16 as a tan oil.

$^1$H NMR (400 MHz, CDCl$_3$) δ 6.78 (d, 1H), 6.33 (s, 1H), 6.21 (d, 1H), 4.59 (s, 2H), 4.21 (q, 2H), 3.8 (s, 3H), 3.45 (bs, 2H), 1.28 (t, 3H).

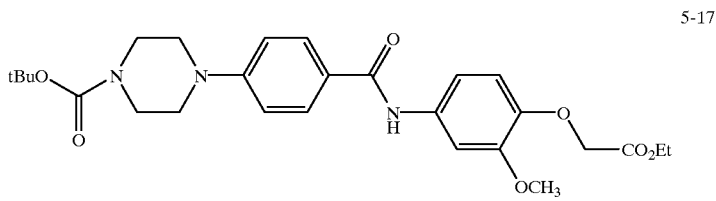
5-17

Ethyl (4-(4-(4-(1,1-dimethylethoxycarbonyl)piperazin-1-yl)phenylcarbonylamino)-2'-(2-methoxy)phenoxy)acetate (5-17)

Acid 1-5 and amine 5-16 were coupled as described for 5-5 to give 5-17 as brown solid after chromatography in 50% EtOAc/hexanes.

R$_f$(50% EtOAc/hexanes)=0.13; $^1$H NMR (400 MHz, CDCl$_3$) δ 7.8 (d, 2H), 7.6 (d, 1H), 6.92 (d, 2H), 6.86 (m, 2H), 4.64 (s, 2H), 4.24 (q, 2H), 3.9 (s, 3H), 3.6 (m, 4H), 3.3 (m, 4H), 1.5 (s, 9H), 1.25 (t, 3H).

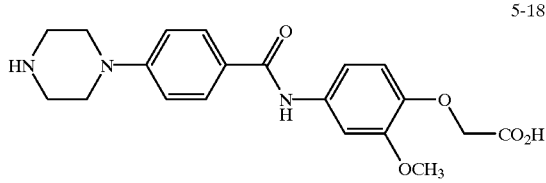
5-18

2-(4-(4-(4-Piperazin-1-yl)phenylcarbonylamino)-2'-(2-methoxy)-phenoxy)acetate (5-18)

Compound 5-17 was treated with LiOH and HCl gas as described for 5-6 to give 5-18 as a white solid after chromatography in 10:1:1 EtOH/H$_2$O/NH$_4$OH.

R$_f$(10:1:1 EtOH/H$_2$O/NH$_4$OH)=0.15; $^1$H NMR (400 MHz, D$_2$O) δ 7.78 (d, 2H), 7.15 (s, 1H), 7.08 (d, 2H), 6.9 (m, 1H), 6.78 (d, 1H), 4.4 (s, 2H), 3.8 (s, 3H), 3.18 (bs, 4H), 2.88 (bs, 4H).

SCHEME 6

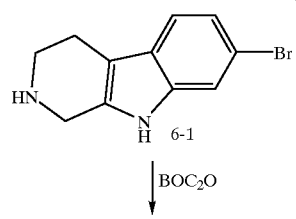
6-1

↓ BOC$_2$O

-continued
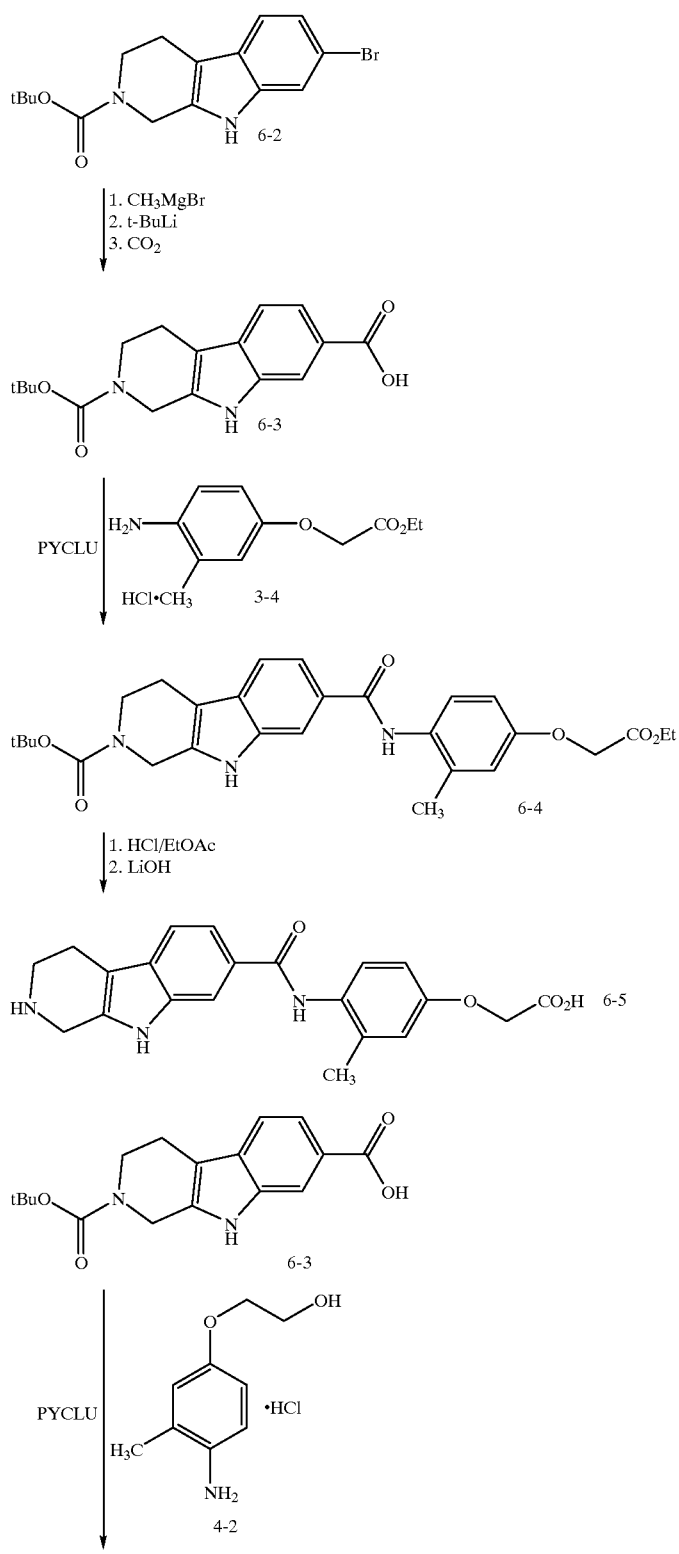

-continued

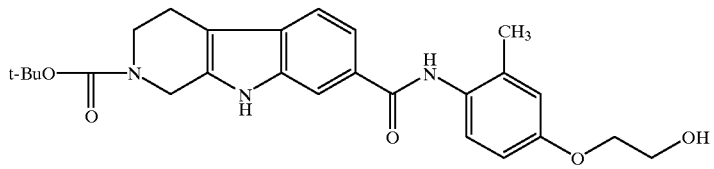

6-6

HCl/EtOAc ↓

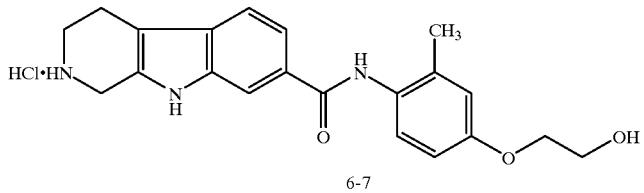

6-7

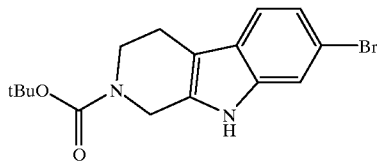

6-2

2-(1,1-Dimethylethoxycarbonyl)-7-bromo 1,2,3,4-tetrahydro-9H-pyrido[3,4-B]indole (6-2)

A suspension of 6-1, prepared by the method of Rinehard et al. (*JACS*, 1987 109, p 3378–3387) (0.366 g, 1.46 mmol) in CH$_2$Cl$_2$ (8 mL) was treated with triethylamine (0.61 mL, 4.4 mmol) followed by di-tert-butyldicarbonate (0.38 g 1.7 mmol) for 1 hour at room temperature. The solution was concentrated and the residue chromatographed (20% EtOAc/hexanes) to give 6-2 as a white solid.

R$_f$ (20% EtOAc/hexanes) 0.28. $^1$H NMR (400 MHz, CDCl$_3$) δ 8.0–7.6 (m, 1H), 7.46 (s, 1H), 7.33 (d, 1H), 7.2 (d, 1H), 4.6 (bs, 2H), 3.78 (bs, 2H), 2.76 (bs, 2H), 1.5 (s, 9H).

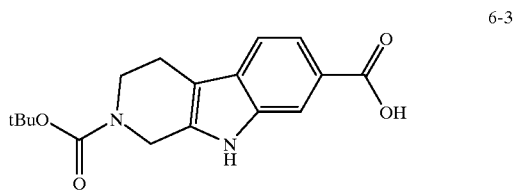

6-3

2-(1,1-Dimethylethoxycarbonyl)-1,2,3,4-tetrahydro-9H-pyrido-[3,4-B]indol-7-yl carboxylic acid (6-3)

A solution of 6-2 (0.26 g, 0.734 mmol) in THF (10 mL) was cooled to 0° C. and treated with methylmagnesium chloride (3.0 M in THF, 0.29 mL, 0.87 mmol) to give a pale yellow solution. After 15 minutes the solution was cooled to −78° C. and treated with tBuLi (1.7M in pentane, 4.35 mL, 7.39 mmol) to give a bright yellow solution. After 10 minutes CO$_2$ gas was bubbled vigorously through the solution for 10 minutes. Saturated NH$_4$Cl, water and enough 6N NaOH to reach pH12 were added and the solution extracted with EtOAc. The EtOAc layer was back extracted with 0.5 NaOH and the aqueous layers combined, acidified to pH 7 and extracted with EtOAc, the EtOAc layer was dried (Na$_2$SO$_4$) filtered and concentrated to give 6-3 as an off-white solid.

R$_f$(75:25:1 CHCl$_3$/MeOH/HOAc)=0.48; $^1$H NMR (400 MHz, DMSO-d$_6$) δ 12.0 bs, 1H), 11.2 (s, 1H), 7.93 (s, 1H), 7.6 (d, 1H), 7.45 (d, 1H), 4.6 (s, 2H), 3.68 (m, 2H), 2.7 (m, 2H), 1.4 (s, 9H).

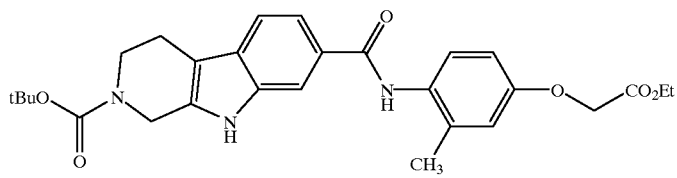

6-4

Ethyl (3-methyl-4-(9-H-2-(1,1-dimethylethoxycarbonyl-1,2,3,4-tetrahydro-9H-pyrido[3,4-B]indol-7-yl-carboxamido)phenoxy)acetic acid (6-4)

A solution of 6-3 (0.078 g, 0.25 mmol) and 3-4 (0.303 g, 1.23 mmol) in CH$_2$Cl$_2$ were treated with diisopropylamine and PYCLU as described for 5—5 to give 6-4 as a white solid after chromatography in a gradient of 40 to 60% EtOAc/hexanes.

R$_f$ (40% EtOAc/hexanes)=0.11; $^1$H NMR (400 MHz, CDCl$_3$) δ 8.5–8.2 (m, 1H), 8.0 (s, 1H), 7.75 (d, 1H), 7.63 (s, 1H), 7.52 (s, 2H), 6.83 (s, 1H), 6.80 (d, 1H), 4.7 (bs, 2H), 4.6 (s, 2H), 4.28 (q, 2H), 3.8 (bs, 2H), 2.83 (bs, 2H), 2.82 (s, 3H), 1.5 (s, 9H), 1.3 (t, 3H).

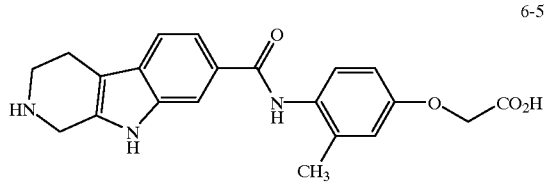
6-5

(3-Methyl-4-(1,2,3,4-tetrahydro-9H-pyrido[3,4-B]indol-7-yl-carboxamido)phenoxy)acetic acid (6-5)

A solution of 6-4 (0.082 g, 0.16 mmol) in EtOAc (10 mL) was treated first with HCl gas, then with LiOH.H$_2$O as described for 5-6 to give 6-5 as a white solid after chromatography in 18:1:1 EtOH/H$_2$O/NH$_4$OH.

R$_f$(18:1:1 EtOH/H$_2$O/NH$_4$OH)=0.48; $^1$H NMR (400 MHz, D$_2$O) δ 7.9 (s, 1H), 7.54 (m, 2H), 7.13 (d, 1H), 6.84 (s, 1H), 6.75 (d, 1H), 4.40 (s, 2H), 3.8 (s, 2H), 3.0 (m, 2H), 2.7 (m, 2H), 2.15 (s, 3H).

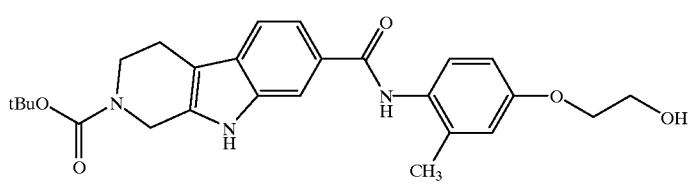
6-6

(3-Methyl-4-(9-H-2-(1,1-dimethylethoxycarbonyl)-1,2,3,4-tetrahydro-9H-pyrido[3,4-B]indol-7-yl-carboxamido)phenoxy)ethanol (6-6)

A solution of 6-3 (0.068 g, 0.214 mmol) and 4-2 (0.213 g, 1.04 mmol) in CH$_2$Cl$_2$ (5 mL) were treated with diisopropylamine and PYCLU as described for 2-5 to give 6-6 as a white solid after chromatography in 100% EtOAc.

R$_f$(100% EtOAc)=0.33; $^1$H NMR (400 MHz, CD$_3$OD) δ 7.98 (s, 1H), 7.65 (d, 1H), 7.5 (d, 1H), 7.2 (d, 1H), 6.9 (s, 1H), 6.82 (d, 1H), 5.5 (s, 1H), 4.66 (s, 2H), 4.05 (m, 2H), 3.87 (m, 2H), 3.8 (m, 2H), 2.7 (m, 2H) 2.3 (s, 3H), 1.5 (s, 9H).

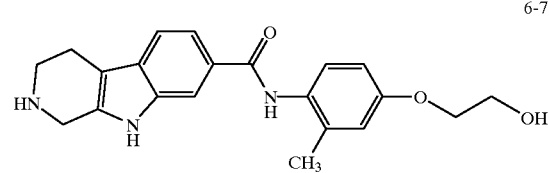
6-7

2-(3-Methyl-4-(1,2,3,4-tetrahydro-9H-pyrido [3,4-B]indol-7-yl-carboxamido)phenoxy)ethanol (6-7)

A suspension of 6-6 in dioxane was treated with HCl gas as described for 5-8 to give 6-7 as a yellow solid after chromatography in 18:1:1 EtOH/H$_2$O/NH$_4$OH.

R$_f$(18:1:1 EtOH/H$_2$O/NH$_4$OH)=0.5; $^1$H NMR (400 MHz, D$_2$O) δ 7.95 (s, 1H), 7.6 (m, 2H), 7.15 (d, 1H), 6.93 (s, 1H), 6.84 (d, 1H), 4.44 (s, 2H), 4.1 (m, 2H), 3.85 (m, 2H), 3.55 (m, 2H), 3.05 (m, 2H), 2.18 (s, 3H).

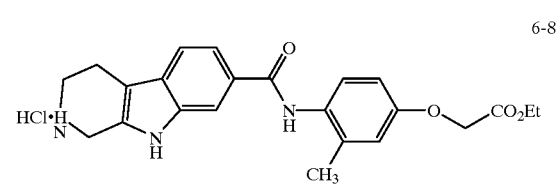
6-8

Ethyl (3-Methyl-4-1,2,3,4-tetrahydro-9H-pyrido[3,4-B]indol-7-yl-carboxamido)phenoxy)acetate hydrochloride (6-8)

A suspension of 6-4 in EtOAc was treated with HCl gas as described for 5-8 to give 6-8 as a yellow solid.

$^1$H NMR (400 MHz, DMSO-d$_6$) δ 11.2 (s, 1H), 9.85 (s, 1H), 9.5 (bs, 1H), 8.05 (s, 1H), 7.7 (d, 1H), 7.57 (d, 1H), 6.85 (s, 1H), 6.75 (d, 1H), 4.78 (s, 2H), 4.4 (bs, 2H), 4.18 (q, 2H), 3.45 (m, 2H), 2.2 (s, 3H), 1.23 (t, 3H).

SCHEME 7
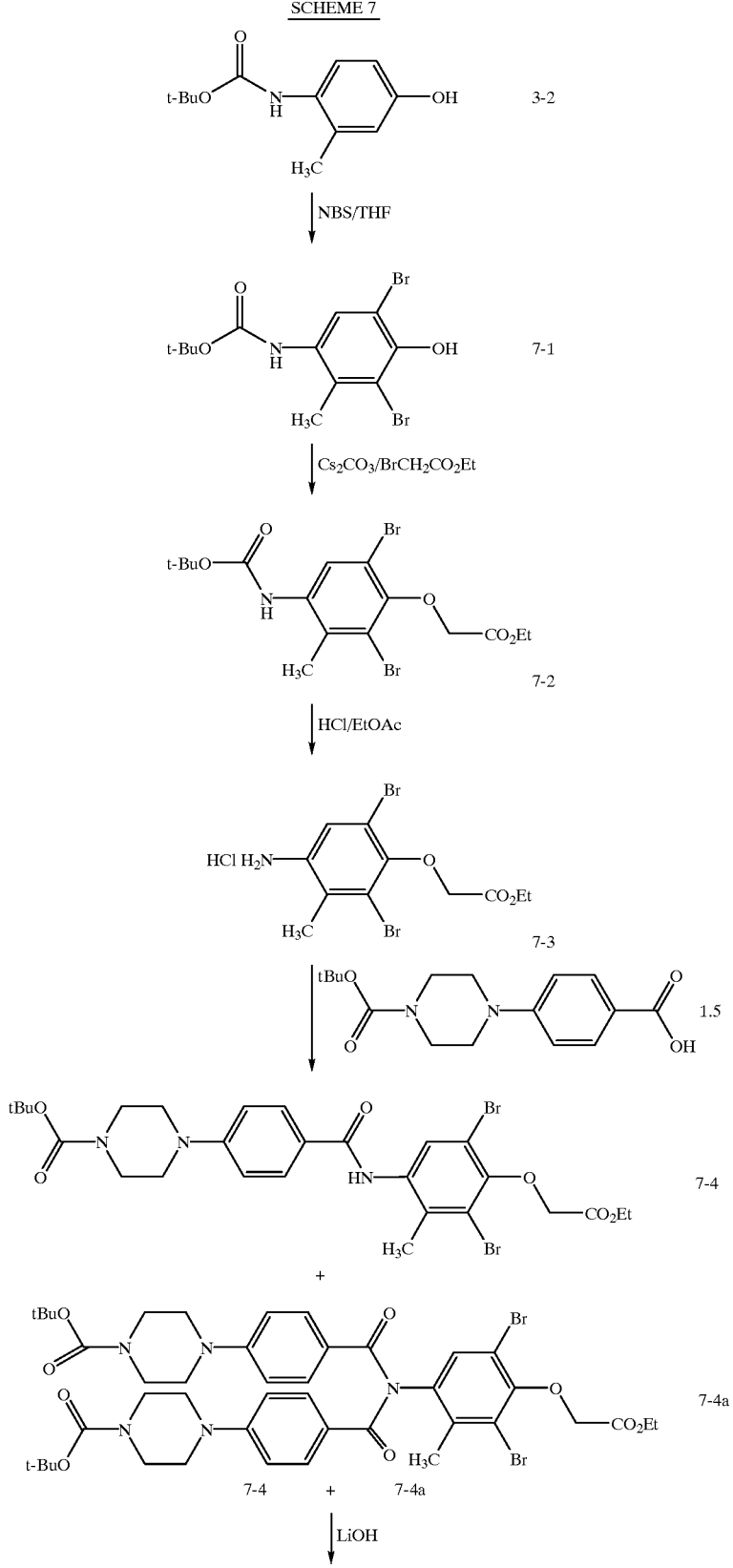

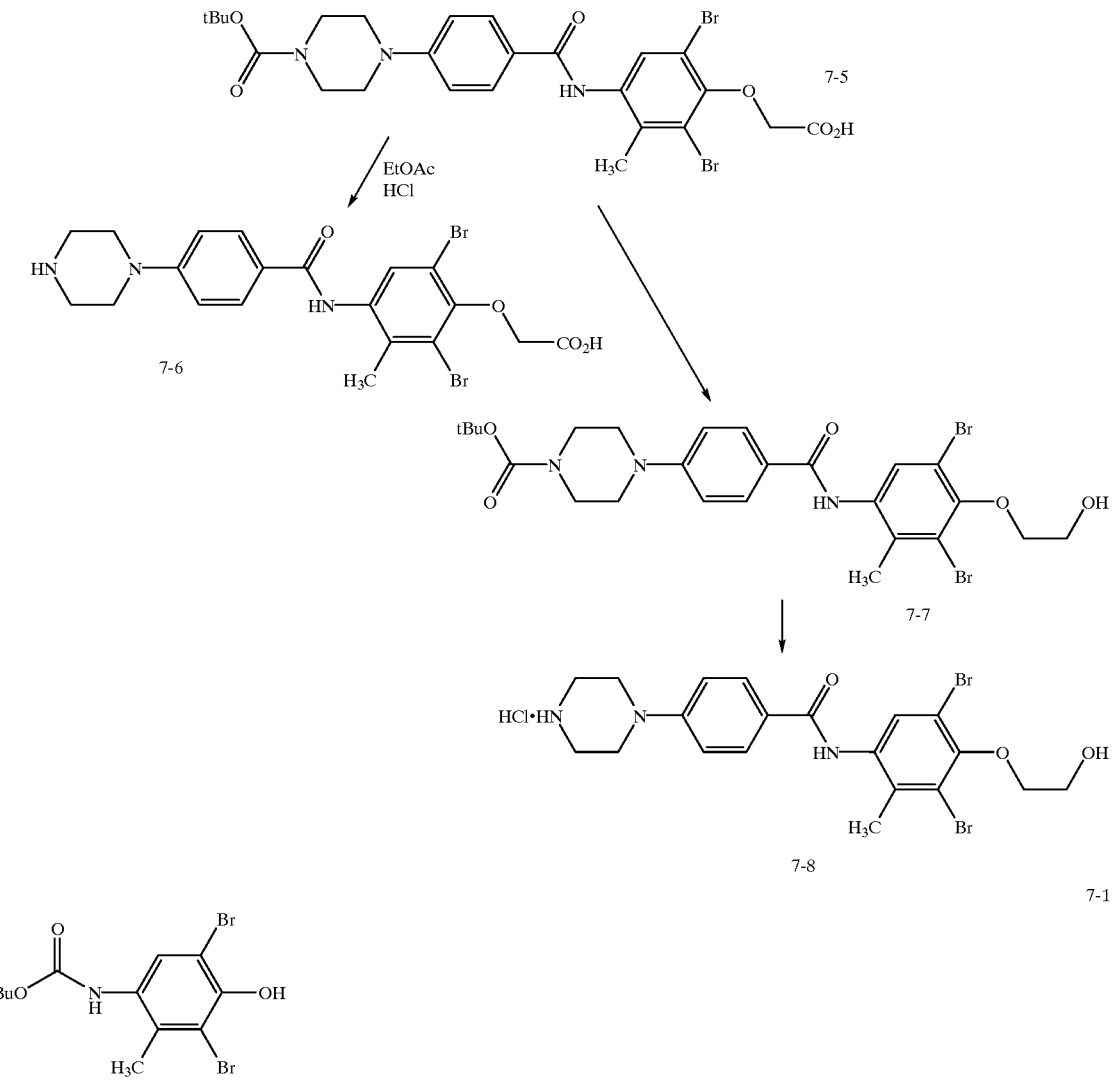

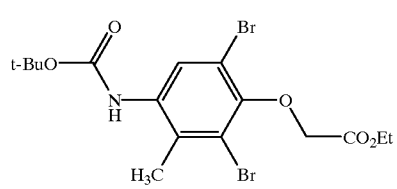

2,6-Dibromo-3-methyl-4-(1,1-dimethylethoxycarbonyl) aminophenol (7-1)

A solution of 3-2 (1.0 g, 450 mmol) in 20 mL THF under argon was treated with N-Bromosuccinimide (1.6 g, 9 mmol) for 2 hr. The solution was concentrated and the residue was resuspended in carbontetrachloride and filtered. The filtrate was concentrated and chromatographed (15% EtOAc/hexanes) to give 7-1 as a white solid.

$R_f$(20% EtOAchexanes)=0.56; $^1$H NMR (400 MHz, CDCl$_3$) δ 7.79 (bs, 1H), 6.08 (bs, 1H), 5.8 (s, 1H), 2.33 (s, 3H), 1.43 (s, 9H).

Ethyl 2-(2,6-dibromo-3-methyl-4-(1,1-dimethylethoxycarbonyl)-aminophenoxy) acetic acid (7-2)

A solution of 7-1 (0.6 g, 1.57 mmol) in DMF was treated with cesium carbonate and ethyl bromo acetate as described for 3-3 to give 7-2 as a tan solid $R_f$(20% EtOAc/hexanes)=0.56; $^1$H NMR (400 MHz, CDCl$_3$) δ 8.0 (bs, 1H), 6.21(bs, 1H), 4.56 (s, 2H), 4.3 (q, 2H), 2.35 (s, 3H), 1.5 (s, 9H), 1.33 (t, 3H).

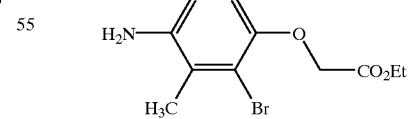

Ethyl (2,6-dibromo-3-methyl-4-aminophenoxy) acetic acid (7-3)

A solution of 7-2 (0.6 g, 1.29 mmol) in EtOAc (10 mL) was cooled to −78° C., saturated with HCl gas, warmed to 0° C. and stifrred for 1 hour, then concentrated at ambient temperature to give 7-3 as a tan solid.

$^1$H NMR (400 MHz, DMSO) δ 7.0 (s, 1H), 4.8–4.4 (b, 2H), 4.41 (s, 2H), 4.2 (q, 2H), 2.18 (s, 3H), 1.2 (t, 3H).

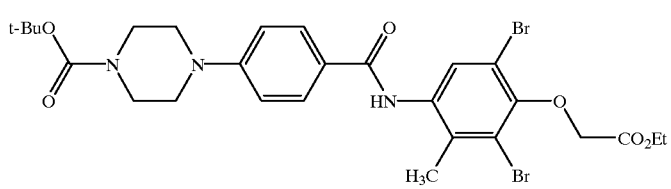

7-4

Ethyl (2,6-dibromo-3-methyl-4-(4-(N-(1,1-dimethylethoxycarbonyl)piperazin-4-yl)phenylcarboxamide)phenoxy) acetic acid (7-4)

A solution of 7-3 (0.520 g, 1.29 mmol) and 1-5 (0.395 g, 1.29 mmol) in $CH_2Cl_2$ was treated with chloro-N,N,N'N',-bis(pentamethylene)formamidinium hexafluorophosphate (0.504 g, 0.1.4 mmol) and diisopropylethyl amine (0.9 mL, 5.16 mmol) and stirred at room temperature for 24 hours. The solution was diluted with EtOAc and washed with $H_2O$, 10% $KHSO_4$, saturated $NaHCO_3$ and brine, dried over $MgSO_4$, filtered and evaporated. The residue was chromatographed (silica gel 30% EtOAc/hexanes) to give a mixture of 7-4 and 7-4a.

$R_f$ 7-4a(50% EtOAc/hexanes)=0.45; $^1$H NMR (400 MHz, $CDCl_3$) δ 8.0 (m, 2H), 7.8 (d, 2H), 7.5 (s, 1H), 6.93 (d, 2H), 6.85 (d, 1H), 4.6 (s, 2H), 4.3 (q, 2H), 3.6 (bs, 8H), 3.35 (m, 8H), 2.4 (s, 3H), 1.45 (s, 9H), 1.35 (t, 3H).

$R_f$ 7-4(50% EtOAc/hexanes)=0.37; $^1$H NMR (400 MHz, $CDCl_3$) δ 7.6 (d, 2H), 6.7 (d, 2H), 4.6 (s, 2H), 4.3 (q, 2H), 3.55 (bs, 4H), 3.3 (bs, 4H), 2.38 (s, 3H), 1.45 (s, 9H), 1.33 (t, 3H).

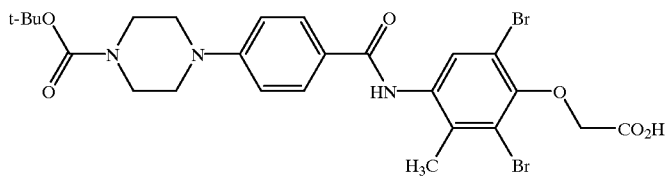

7-5

2-(2,6-Dibromo-3-methyl-4-(4-(N-(1,1-dimethylethoxycarbonyl)-piperazin-4-yl)phenylcarboxamide) phenoxy) acetic acid (7-5)

A solution of 7-4 and 7-4a (0.3 g) in 1:1:1 THF/MeOH/$H_2O$ was treated with LiOH (0.084 g, 2 mmol) at 60° C. After 1 hour the reaction was diluted with EtOAc and 10% $KHSO_4$ and the layers were separated. The organic layer was washed with $H_2O$, brine, dried with $MgSO_4$, filtered and evaporated to give 7-5 as a clear oil after chromatography in 9:0.5:0.5 $CH^2Cl_2$/MeOH/HOAc.

$R_f$(9:0.5:0.5 $CHCl_3$/MeOH/HOAc)=0.6; $^1$H NMR (400 MHz, CD3OD) δ 7.90 (d, 2H), 7.6 (s, 2H), 7.05 (d, 2H), 4.55 (s, 2H), 3.6 (bs, 4H), 3.3 (bs, 4H), 2.35 (s, 3H), 1.5 (s, 9H).

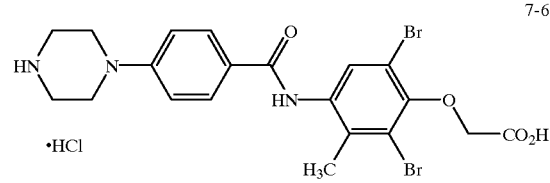

7-6

(2,6-Dibromo-3-methyl-4-(4-piperazin-4-yl) phenylcarboxamide)phenoxy) acetic acid hydrochloride (7-6)

A slurry of the intermediate acid (0.4 g, 0.6 mmol) in EtOAc was cooled to −78° C. and saturated with HCl gas. The reaction was warmed to 0° C., then concentrated in vacuo to give 7-6 as the HCl salt.

$R_f$(10:0.5:0.5 EtOH/$H_2O$/$NH_4OH$)=0.18; $^1$H NMR (400 MHz, $D_2O$) δ 7.73 (d, 2H), 7.23 (s, 1H), 7.02 (d, 2H), 4.3 (s, 2H), 3.1 (bs, 4H), 2.82 (bs, 4H), 2.1 (s, 3H).

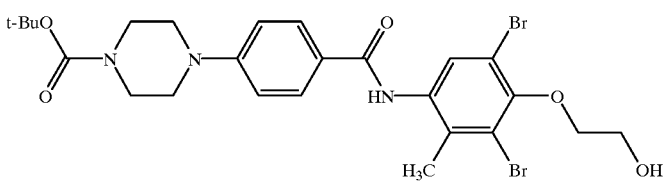

7-7

2-(2,6-Dibromo-3-methyl-4-(4-(N-(1,1-dimethylethoxycarbonyl)-piperazin-4-yl)phenylcarboxamide) phenoxy) ethanol (7-7)

A solution of 7-4 (0.2 g, 0.32 mmol) in THF (5 mL) was cooled to 0° C. and treated with Borane (1M in THF, 3.2 mL, 3.2 mmol) and stirred at room temperature for 48 hours. An additional 3.2 mL of Borane solution was added and after 15 minutes the reaction was quenched with MeOH, stirred for 0.5 hour, concentrate, the residue was dissolved in EtOAc and washed with 10% KHSO$_4$, brine, dried over MgSO$_4$, filtered and evaporated to give 7-7 as a white solid.

R$_f$(50% EtOAc/hexanes)=0.42; $^1$H NMR (400 MHz, CDCl$_3$) δ 7.8 (d, 2H), 7.5 (s, 1H), 6.94 (d, 2H), 4.2 (m, 2H), 4.0 (m, 2H), 3.6 (m, 4H), 3.3 (m, 4H), 2.4 (s, 3H), 1.45 (s, 9H).

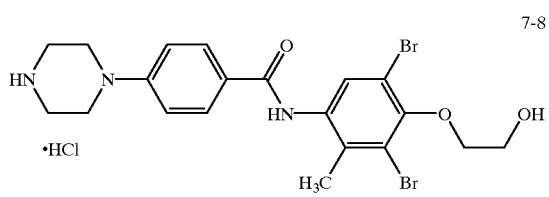

2-(2,6-Dibromo-3-methyl-4-(4-(piperazin-4-yl) phenylcarboxamide)phenoxy) ethanol hydrochloride (7-8)

A solution of 7-7 (0.15 g, 0.24 mmol) in dioxane was treated with HCl gas as described for 7-5 to give 7-8 as a white solid.

R$_f$(10% MeOH/CHCl$_3$ saturated with NH3)=0.31; $^1$H NMR (400 MHz, CD$_3$OD) δ 7.85 (d, 2H), 7.59 (s, 1H), 7.02 (d, 1H), 4.1 (m, 2H), 3.95 (m, 2H), 3.0 (m, 4H), 2.54 (s, 3H).

SCHEME 8

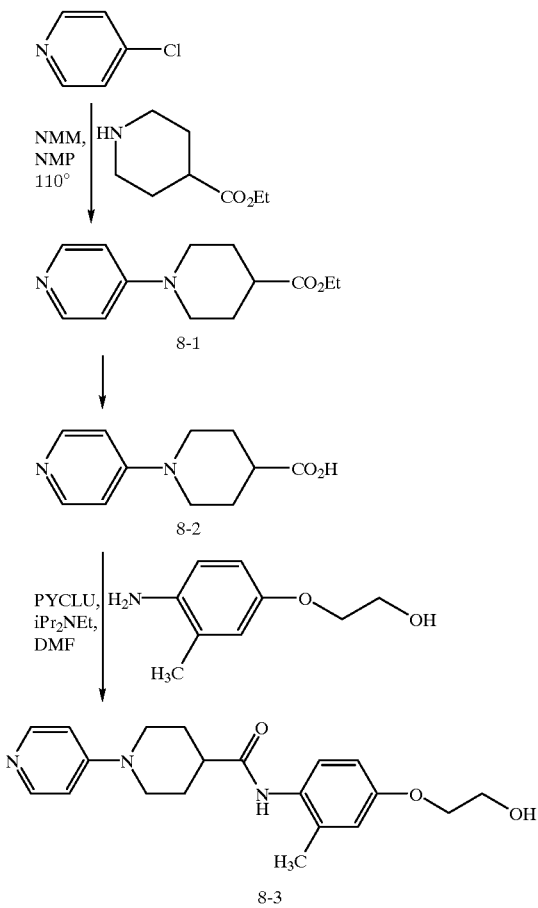

Ethyl 4-pyridylpiperidin-4-ylcarboxylate (8-1)

Ethyl isonipecotate (6.0 g, 38.66 mmol), 4-chloropyridine hydrochloride (5.9 g, 38.66 mmol) and N-methylmorpholine (9.3 g mL, 85.00 mmol), were dissolved in N-methylpyrrolidine (50 mL) and the resulting solution was heated at 100° C. for 48 h. The solution was concentrated in vacuo and the residue was dissolved in EtOAc and washed with water and brine (2×100 mL), then dried (Na2SO4) and evaporated. The resulting residue was purified by flash chromatography (5% MeOH/CHC13) to afford 8-1 as a crystalline solid.

$^1$H NMR (CDCl$_3$) δ 8.21 (d, j=6.8 Hz, 2H), 6.78 (d, j=6.8 Hz, 2H), 4.18 (q, j=7.0 Hz, 2H), 3.85 (m, 2H), 3.10 (m, 2H), 2.61 (m, 1H), 2.05 (m, 2H), 1.85 (m, 2H), 1.23 (t, j=7.0 Hz, 3H).

4-Pyridylpiperidin-4-ylcarboxylic acid (8-2)

A solution of 8-1 (10 g, 42.7 mmol) in THF (50 mL) was teated with 1N LiOH (47 mL, 47.0 mmol) and water (50 mL). The resulting solution was stirred at ambient temperature for 12 h. The solution was concentrated and the aqueous residue was cooled to 0° C., then adjusted to pH=6 with 1N HCl. The resulting solid was collected by filtration and dried in vacuo to afford 8-1 as a white solid.

$^1$H NMR (D$_2$O) δ 7.95 (d, j=6.8 Hz, 2H), 6.73 (d, j=6.8 Hz, 2H), 3.76 (d, j=12.8 Hz, 2H), 2.81 (m, 2H), 2.20 (m, 1H), 1.85 (d, j=12.9 Hz, 2H), 1.55 (m, 2H).

N-(4-Pyridyl)piperidin-4-carbonylamino-3-methylphenoxyethanol (8-3)

A solution of 2-(3-methyl-4-aminophenoxy)ethanol (24) (0.29 g, 1.41 mmol), 4-(pyridyl)(piperidin)-4-carboxylic acid (0.30 g, 1.41 mmol), chloro-N, N, N', N'-bis (pentamethylene)formamidinium hexafluorophosphate (0.50 g, 1.41 mmol), and diisopropylamine (0.25 mL, 1.41 mmol) in dimethylformamide (15 mL) was stirred at ambient temperature for 48 h and the solvent removed in vacuo to give an oil. This material was chromatographed on silica gel using 5:95 methanolammonia saturated chloroform as eluant to give 8-3 as an off-white solid.

$^1$H NMR (CD$_3$OD): δ 8.10 (d, j=6.6 Hz, 2H), 7.11 (d, j=8.6 Hz, 2H), 6.87 (d, j=6.6 Hz, 2H), 6.83 (s, 1H), 6.77 (d, j=8.6 Hz, 2H), 4.10 (d, j=13.4 Hz, 2H), 4.02 (t, j=4.6 Hz, 2H), 3.85 (t, j=4.9 Hz, 2H), 3.01 (t, j=12.5 Hz, 2H), 2.72 (m, 1H), 2.20 (s, 3H), 1.98 (d, j=13.2 Hz, 2H), 1.84 (m, 2H).

EXAMPLE 9

Tablet Preparation

Tablets containing 25.0, 50.0, and 100.0 mg., respectively, of the prodrug 2-(3-Methyl-4-(4-(1-piperazinyl) phenylcarbonylamino)phenoxy)-ethanol hydrochloride are prepared as illustrated below:

| TABLE FOR DOSES CONTAINING FROM 25–100 MG OF THE PRODRUG | | | |
|---|---|---|---|
| | Amount-mg | | |
| Prodrug | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 10

Intravenous Formulations

An intravenous dosage form of the above-indicated prodrug is prepared as follows:

| | |
|---|---|
| Prodrug | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc. (Rockville, Md., copyright 1994).

EXAMPLE 11

Intravenous Formulation

A pharmaceutical composition was prepared at room temperature using 2-(3-Methyl-4-(4-(1-piperazinyl) phenylcarbonylamino)phenoxy)-ethanol hydrochloride, a citrate buffer, and sodium chloride, to obtain a concentration of of 0.25 mg/ml.

800 grams of water was introduced into a standard pharmaceutical mixing vessel. 0.25 grams of 2-(3-Methyl-4-(4-(1-piperazinyl)phenylcarbonylamino)phenoxy)-ethanol hydrochloride was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| 2-(3-Methyl-4-(4-(1-piperazinyl)phenylcarbonyl-amino)phenoxy)-ethanol hydrochloride | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transfered to an infusion bag.

Diborane Reduction

Additional alcohol prodrugs of the present invention can be prepared according to the procedure whereby diborane is used to reduce the acid to the corresponding alcohol:

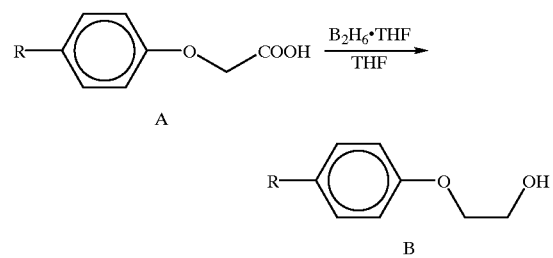

According to the procedure, 1 mmol of acid A and 50 mmL of distilled dry THF is added to an oven dried round bottomed flask with a stirring bar, septum, condenser and argon inlet to form a solution. This solution is cooled in an ice bath and one molar equivalent of borane-THF comple as a 1M solution in THF is added with a syringe over 5 min. The cooling bath is allowed to expire and the mixture is stirred at ambient temperature until the reduction is complete. The reaction is quenched with methanol and the resulting mixture is stirred one hour. The solvents are removed in vacuo and the residue is chromatographed on silica gel to provide the desired alcohol B.

Exemplary starting materials (A) for the diborane reaction are shown in the following table:

| A | Source |
|---|---|
| | EP 381 033 |
| | EP 381 033 |

-continued
| A | Source |
|---|---|
| 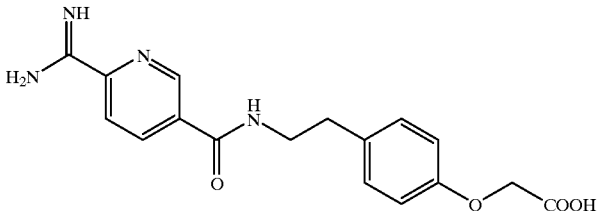 | U.S. Pat. No. 5,256,812 |
| 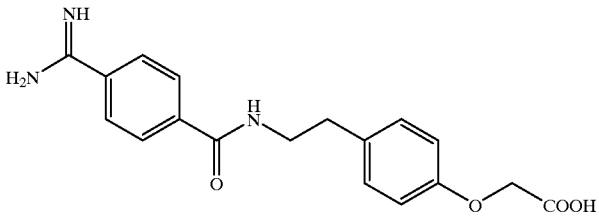 | EP 381 033 |
| 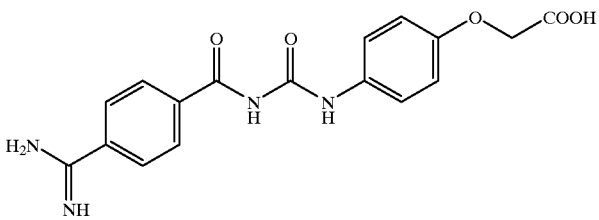 | EP 632 019 |
| 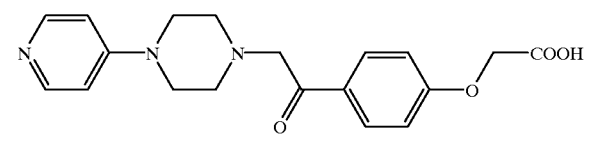 | WO 94/22834 |
| 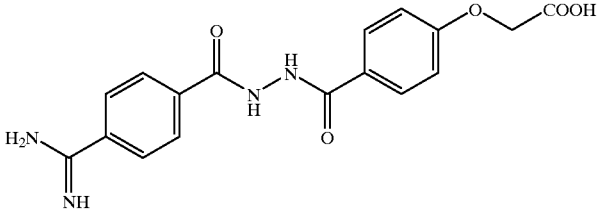 | EP 632 016 |
| 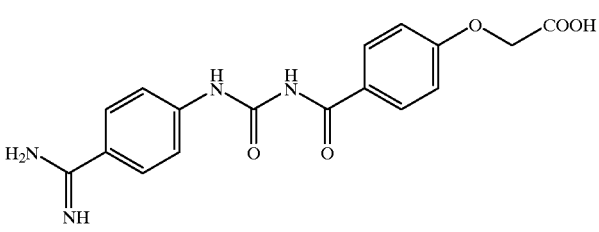 | EP 632 020 |
| 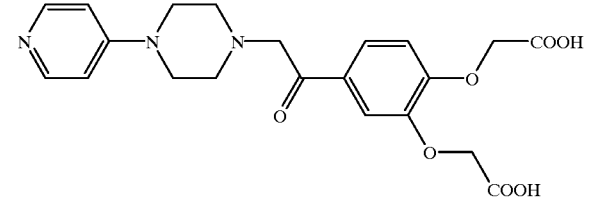 | WO 94/22835 |

-continued

| A | Source |
|---|---|
| [structure: 4-amidinophenyl-imidazolidinone-phenoxyacetic acid] | EP 503 548 |
| [structure: 4-amidinophenyl-thiadiazolidine dioxide-phenoxyacetic acid] | EP 503 548 |
| [structure: 4-amidinophenoxy-methyl-benzimidazole-oxyacetic acid] | EP 531 883 |
| [structure: N-methylpiperidinyl-hydroxy-trimethoxyphenyl chalcone phenoxyacetic acid] | EP 659743 |
| [structure: N-methylpiperidinyl-hydroxy-phenyl chalcone phenoxyacetic acid] | EP 659743 |
| [structure: N-methylpiperidinyl-trimethoxyphenyl chalcone phenoxyacetic acid] | EP 659743 |
| [structure: N-methylpiperidinyl-phenyl propanone phenoxyacetic acid] | EP 659743 |

| A | Source |
|---|---|
| (structure) | JP 7138221 |
| (structure) | JP 7179407 |
| (structure) | WO 94/14775 |
| (structure) | WO 94/14775 |
| (structure) | WO 94/15913 |
| (structure) | WO 94/22440 |

| A | Source |
|---|---|
| 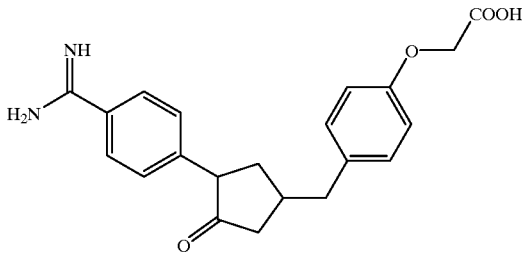 | EP 623615 |
| 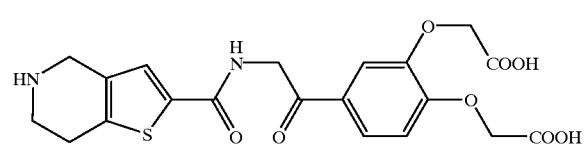 | WO 94/21599 |
| 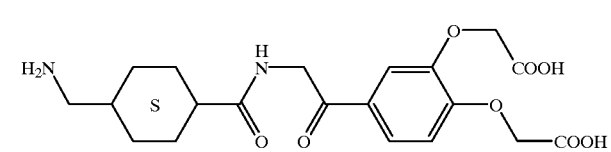 | WO 94/21599 |
| 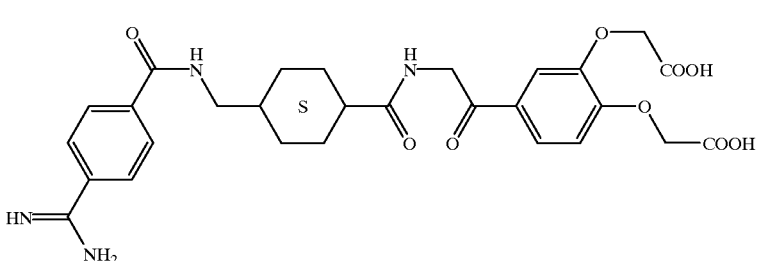 | WO 94/21599 |
| 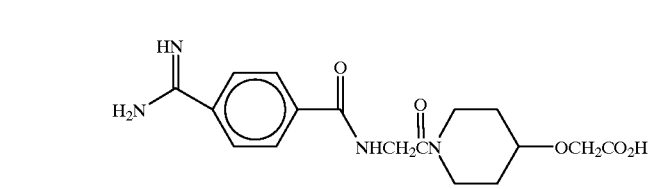 | EP 0 505 868 |
| 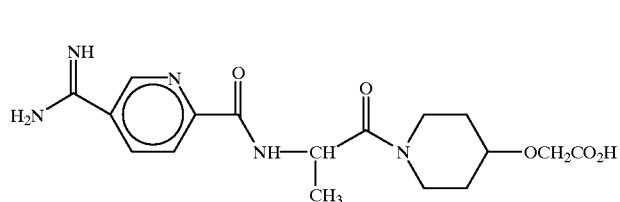 | EP 0 505 868 |
| 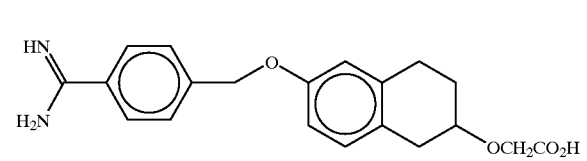 | EP 0 635 492 |
| 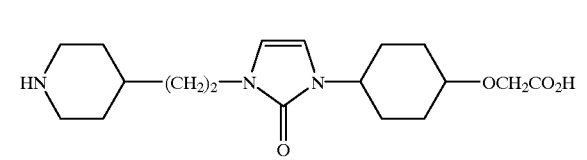 | EP 0 587 134 |

| A | Source |
|---|---|
| 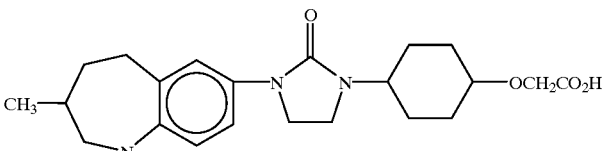 | EP 0 612 741 |
| 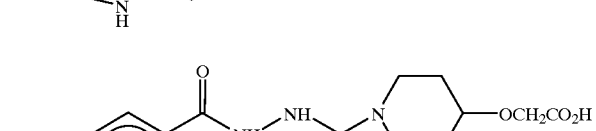 | EP 0 632 016 |
| 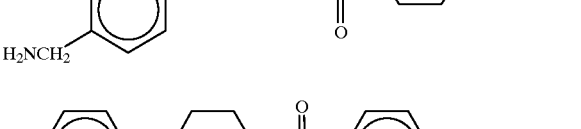 | WO 94/22835 |

THERAPEUTIC TREATMENT

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A compound having the formula $$X—Y—Z—A—B$$

or a pharmaceutically acceptable salt thereof, wherein

X is piperazine, piperidine, pyridine or phenyl;
Y is piperazine, piperidine, pyridine or phenyl;

Z is

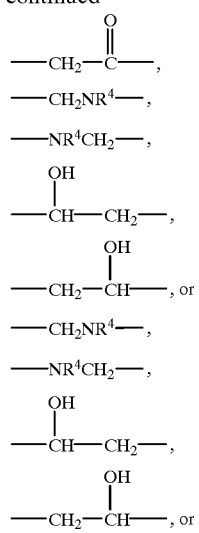

Z represents a bond;
$R^4$ is selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-4}$ alkoxy,
  $C_{1-4}$ alkoxy $C_{1-6}$ alkyl,
  carboxy,
  carboxy $_{1-6}$ alkyl,
  $C_{1-3}$ alkoxycarbonyl, $C_{1-3}$ alkoxycarbonyl $C_{1-6}$ alkyl,
carboxy $C_{1-6}$ alkyloxy,
hydroxy, and
hydroxy $C_{1-6}$ alkyl;

A is
a 5 or 6 membered aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl, or
a 9 or 10 membered fused aromatic ring, having 0, 1, 2 or 3 heteroatoms selected from N, O, and S, and either unsubstituted or monosubstituted on carbon and nitrogen atoms with $R^5$, disubstituted on carbon and nitrogen atoms with $R^5$ and $R^6$, or trisubstituted on carbon and nitrogen with $R^5$, $R^6$, and $R^9$, where $R^5$, $R^6$, and $R^9$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl;

B is

—O(CH$_2$)$_n$CH$_2$OR$^8$,

—CH$_2$(CH$_2$)$_m$CH$_2$OR$^8$, or

—CH(CH$_2$)$_m$CH$_2$OR$^8$,
   |
   R$^7$ wherein n is 1 or 2, and m is 0, 1, or 2;
$R^7$ is selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl;
$R^8$ is selected from the group consisting of
hydrogen,
—C(O)—$C_{1-8}$alkyl,
—C(O)—$C_{3-8}$cycloalkyl,
—C(O)-aryl, and
—C(O)—$C_{1-3}$alkylaryl.

2. A compound of claim 1 having the formula

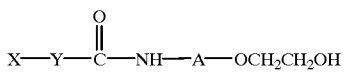

or a pharmaceutically acceptable salt thereof, wherein

A is a 6-membered aromatic ring unsubstituted, monosubstituted with a moiety selected from the group consisting of halogen, $C_{1-3}$alkyl, and $C_{1-3}$alkylsulfonylamino, disubstituted with one or more moieties, same or different, selected from the group consisting of halogen, $C_{1-3}$alkyl, and $C_{1-3}$alkylsulfonylamino or trisubstituted with one or more moieties, same or different, selected from the group consisting of halogen, $C_{1-3}$alkyl, and $C_{1-3}$alkylsulfonylamino.

3. A compound of claim 2 having the formula

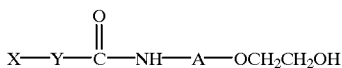

or a pharmaceutically acceptable salt thereof, wherein

A is a 6-membered aromatic ring unsubstituted, monosubstituted with a moiety selected from the group consisting of Br, CH$_3$, and NHSO$_2$CH$_3$, disubstituted with one or more moieties, same or different, selected from the group consisting of Br, CH$_3$, and NHSO$_2$CH$_3$, or trisubstituted with one or more moieties, same or different, selected from the group consisting of Br, CH$_3$, and NHSO$_2$CH$_3$.

4. A compound of claim, 3 having the formula

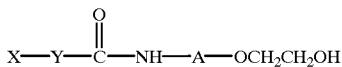

and pharmaceutically acceptable salts, wherein

X is

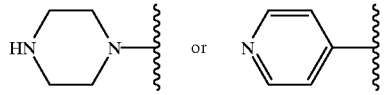

Y is

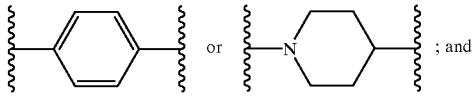 ; and

A is

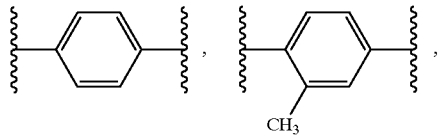 ,

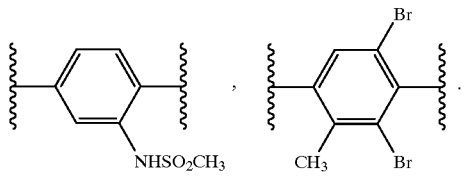 .

5. A compound of claim 4 selected from the group consisting of
2-(4-(4-(1-Piperazinyl)phenylcarbonylamino)phenoxy) ethanol,
2-(3-Methyl-4-(4-(1-piperazinyl)phenylcarbonylamino )phenoxy)-ethanol,
2-(4-(4-(4-piperazin-1-yl)phenylcarbonylamino)-2-methanesulfonyl-aminophenoxy)ethanol,
2-(3-methyl-4-1,2,3,4-tetrahydro-9H-pyrido[3,4-B]indol-7-yl-carboxamido)phenoxy)ethanol,
2-(2,6-Dibromo-3-methyl-4-(4-(piperizin-4-yl) phenylcarbox-amide)phenoxy) ethanol, and
N-(4-Pyridyl)piperidin-4-carbonylamino-3-methylphenoxyethanol,
and pharmaceutically acceptable salts thereof.

6. A composition comprising a compound of claim 1 and a pharmaceutically acceptable carrier.

7. A method for inhibiting the binding of fibrinogen to blood platelets in a mammal, comprising treating the mammal with a composition of claim 6.

8. A method for inhibiting the aggregation of blood platelets in a mammal, by blocking fibrinogen from acting at its receptor site, comprising treating the mammal with a composition of claim 6.

9. A composition for inhibiting the aggregation of blood platelets in a mammal, comprising an efficacious amount of a compound of claim 1 in combination with one or more agents selected from a thrombolytic agent, an anticoagulant agent, and an antiplatelet agent and a pharmaceutically acceptable carrier.

10. A method for inhibiting the aggregation of blood platelets in a mammal, by blocking fibrinogen from acting at its receptor site, comprising treating the mammal with a composition of claim 9.

11. A method for inhibiting osteoclast mediated bone resorption, comprising treating the mammal with a composition of claim 6.

* * * * *